United States Patent
Pu et al.

(10) Patent No.: US 11,858,977 B2
(45) Date of Patent: Jan. 2, 2024

(54) MODIFIED TCR AND USES THEREOF

(71) Applicants: Innovative Cellular Therapeutics Holdings, Ltd., Grand Cayman (KY); Innovative Cellular Therapeutics, Inc., Rockville, MD (US)

(72) Inventors: Chengfei Pu, Shanghai (CN); Dongqi Chen, Shanghai (CN); Xiaogang Shen, Shanghai (CN)

(73) Assignees: Innovative Cellular Therapeutics Holdings, Ltd., George Town (KY); Innovative Cellular Therapeutics, Inc., Rockville, MD (US)

( * ) Notice: Subject to any disclaimer, the term of this patent is extended or adjusted under 35 U.S.C. 154(b) by 323 days.

(21) Appl. No.: 17/077,451

(22) Filed: Oct. 22, 2020

(65) Prior Publication Data
US 2021/0122802 A1    Apr. 29, 2021

Related U.S. Application Data

(60) Provisional application No. 62/929,529, filed on Nov. 1, 2019, provisional application No. 62/925,462, filed on Oct. 24, 2019.

(51) Int. Cl.
*C07K 14/725* (2006.01)
*C07K 14/705* (2006.01)

(52) U.S. Cl.
CPC .... *C07K 14/7051* (2013.01); *C07K 14/70521* (2013.01); *C07K 14/70578* (2013.01); *C07K 2319/02* (2013.01); *C07K 2319/03* (2013.01); *C07K 2319/30* (2013.01); *C07K 2319/33* (2013.01)

(58) Field of Classification Search
CPC .......... C07K 14/7051; C07K 14/70521; C07K 14/70578; C07K 2319/02; C07K 2319/03; C07K 2319/30; C07K 2319/33
See application file for complete search history.

(56) References Cited

PUBLICATIONS

Van der Merwe, P., Dushek, O. Mechanisms for T cell receptor triggering. Nat Rev Immunol 11, 47-55. https://doi.org/10.1038/nri2887 (Year: 2011).*
Magee, Michael S., et al. "Human GUCY2C-targeted chimeric antigen receptor (CAR)-expressing T cells eliminate colorectal cancer metastases." Cancer immunology research 6.5: 509-516. (Year: 2018).*
Miyao, Kotaro, et al. "Introduction of Genetically Modified CD37 Improves Proliferation and Persistence of Antigen-Specific CTLsAdapter Molecule Gene Insertion Improves Persistence of CTLs." Cancer immunology research 6.6: 733-744. (Year: 2018).*
"CD134." Wikipedia, Wikimedia Foundation, Dec. 10, 2022, https://en.wikipedia.org/wiki/CD134. (Year: 2022).*
Xingyuan M, Wenyun Z, Tianwen W. Leukocyte function-associated antigen-1: structure, function and application prospects. Protein Pept Lett.; 13(4):397-400. doi: 10.2174/092986606775974429. PMID: 16712517.(abstract) (Year: 2006).*
Bitra A, et al. "Crystal structures of the human 4-1BB receptor bound to its ligand 4-1BBL reveal covalent receptor dimerization as a potential signaling amplifier." J Biol Chem. Jun. 29;293(26):9958-9969. doi: 10.1074/jbc.RA118.003176. Epub May 2, 2018. PMID: 29720398; PMCID: PMC6028974. (Year: 2018).*
Zhao L. CD33 in Alzheimer's Disease—Biology, Pathogenesis, and Therapeutics: A Mini-Review. Gerontology. 2019;65(4):323-331. doi: 10.1159/000492596. EpubDec 12. PMID: 30541012. (Year: 2018).*
Chen W, Zhang Z, Zhang S, Zhu P, Ko JK, Yung KK. MUC1: Structure, Function, and Clinic Application in Epithelial Cancers. Int J Mol Sci.Jun. 18;22(12):6567. doi: 10.3390/ijms22126567. PMID: 34207342; PMCID: PMC8234110. (Year: 2021).*
Miyao, Kotaro, et al. (Cancer immunology research 6.6 (2018): 733-744) (Year: 2018).*

* cited by examiner

*Primary Examiner* — Marcia S Noble
*Assistant Examiner* — Josephine M Gonzales
(74) *Attorney, Agent, or Firm* — Lee & Hayes P.C.

(57) ABSTRACT

Embodiments relate to a modified cell engineered to comprise a modified TCR-CD3 complex, wherein the CD3γ, ζ-chain, CD3ε, and/or CD3δ chains of the modified TCR-CD3 complex are linked to one or more co-stimulatory signaling domains.

18 Claims, 13 Drawing Sheets

Specification includes a Sequence Listing.

MODIFIED TCR AND USES THEREOF

CROSS REFERENCE TO RELATED APPLICATIONS

This application claims the benefit of U.S. Provisional Application 62/925,462, filed Oct. 24, 2019, and U.S. Provisional Application 62/929,529, filed Nov. 1, 2019, which are hereby all incorporated by reference in their entirety.

SEQUENCE LISTING INFORMATION

A computer-readable textfile, entitled "Sequence Listing.txt," created on or about Oct. 21, 2020, with a file size of about 25 KB, contains the sequence listing for this application and is hereby incorporated by reference in its entirety.

TECHNICAL FIELD

The present disclosure relates to compositions and methods of using T cell therapy to treat diseases including cancer.

BACKGROUND

Although great results have been achieved using cellular immunotherapy, some malignant tumors remain untreatable using cell therapy, and cell therapy can cause side effects in some treatments. During CAR T cell therapy, physicians draw patients' blood and harvest their cytotoxic T cells. The cells are re-engineered in a lab to attack the patients' particular cancerous cells. Recent progress in genome editing technologies has allowed scientists to disrupt gene expression in T cells to enhance effector functions or to bypass tumor immune suppression and metabolically hostile tumor microenvironment. Thus, there is a need to modulate T cells in cell therapy to overcome these problems.

SUMMARY

Embodiments relate to a modified cell engineered to a modified component of TCR-CD3 complex, which comprises CD3γ, ζ-chain, CD3ε, and/or CD3δ linked to one or more co-stimulatory signaling domains.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

DETAILED DESCRIPTION

Figure 1:
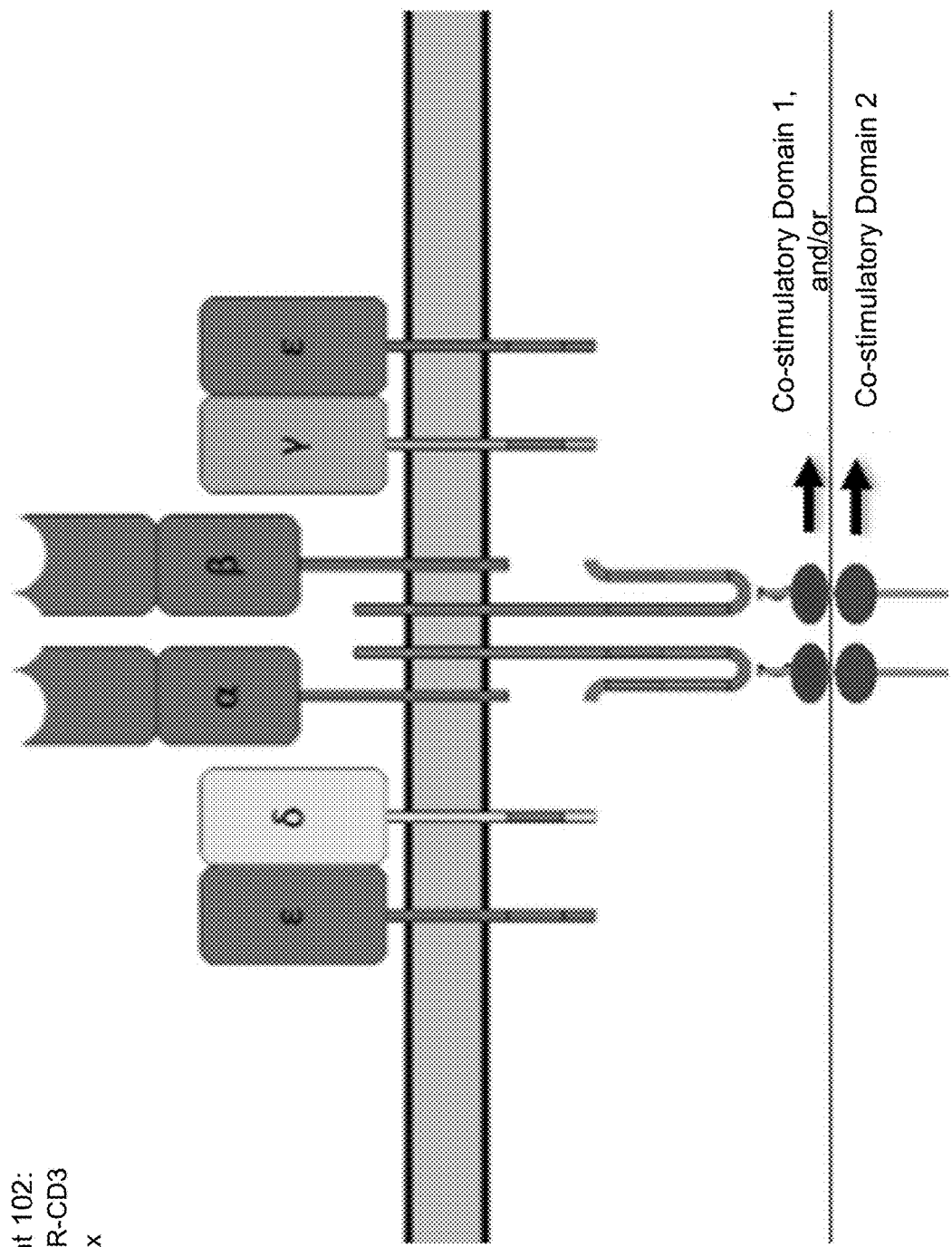
FIGS. 1, 2, 3, and 4 show a schematic diagram of examples of a modified component of the TCR-CD3 complex.
Figure 2:
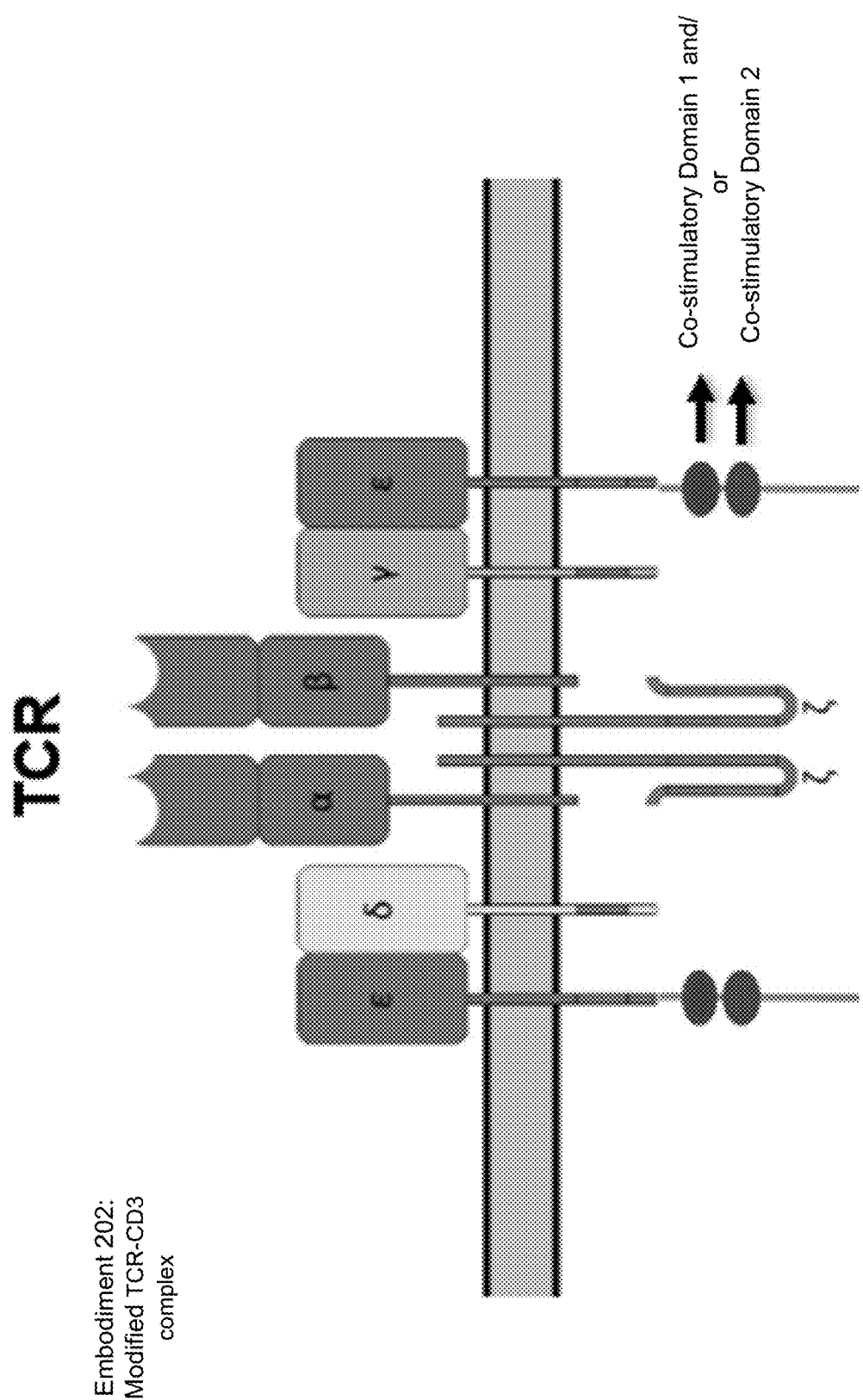
Figure 3:
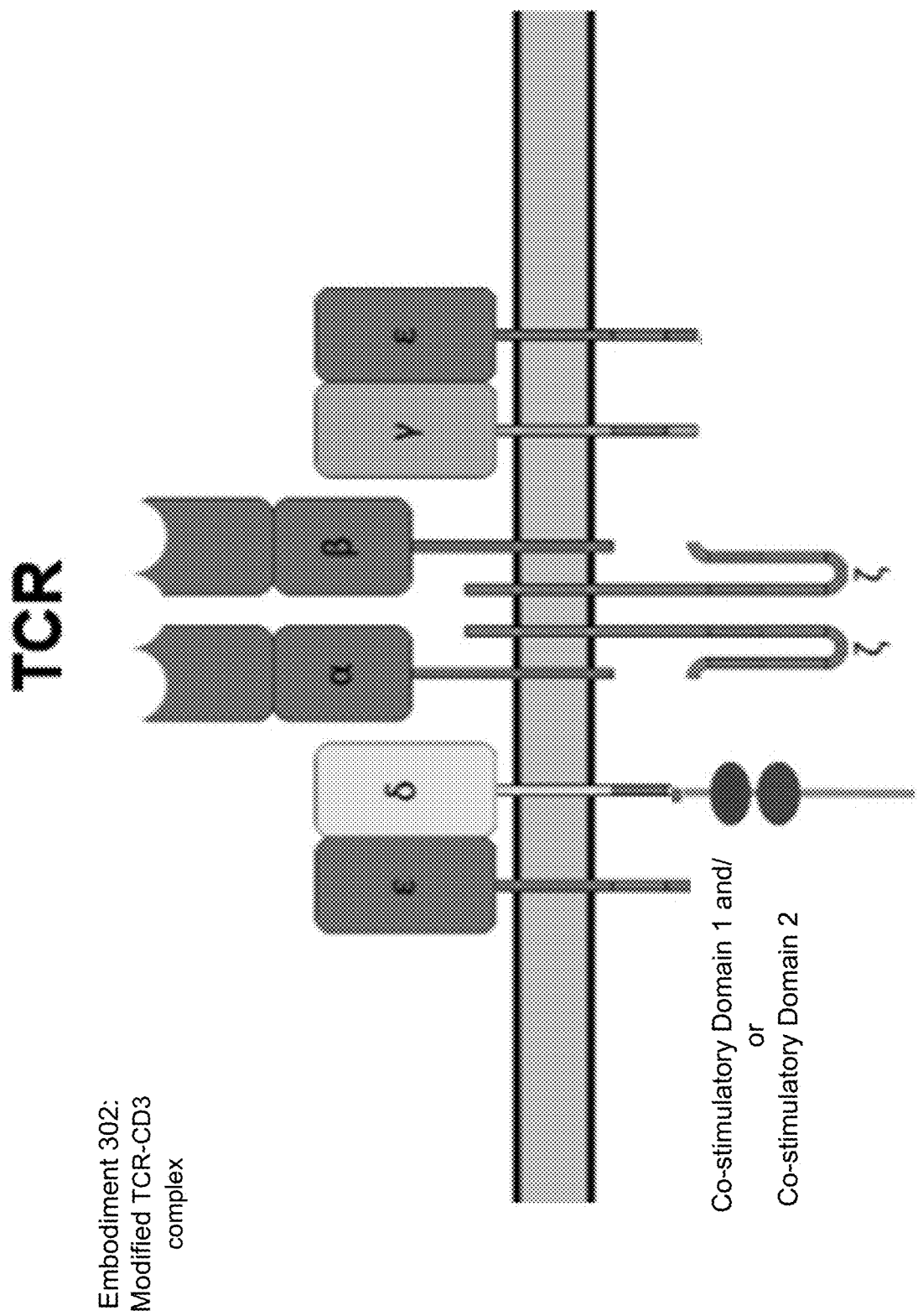
Figure 4:
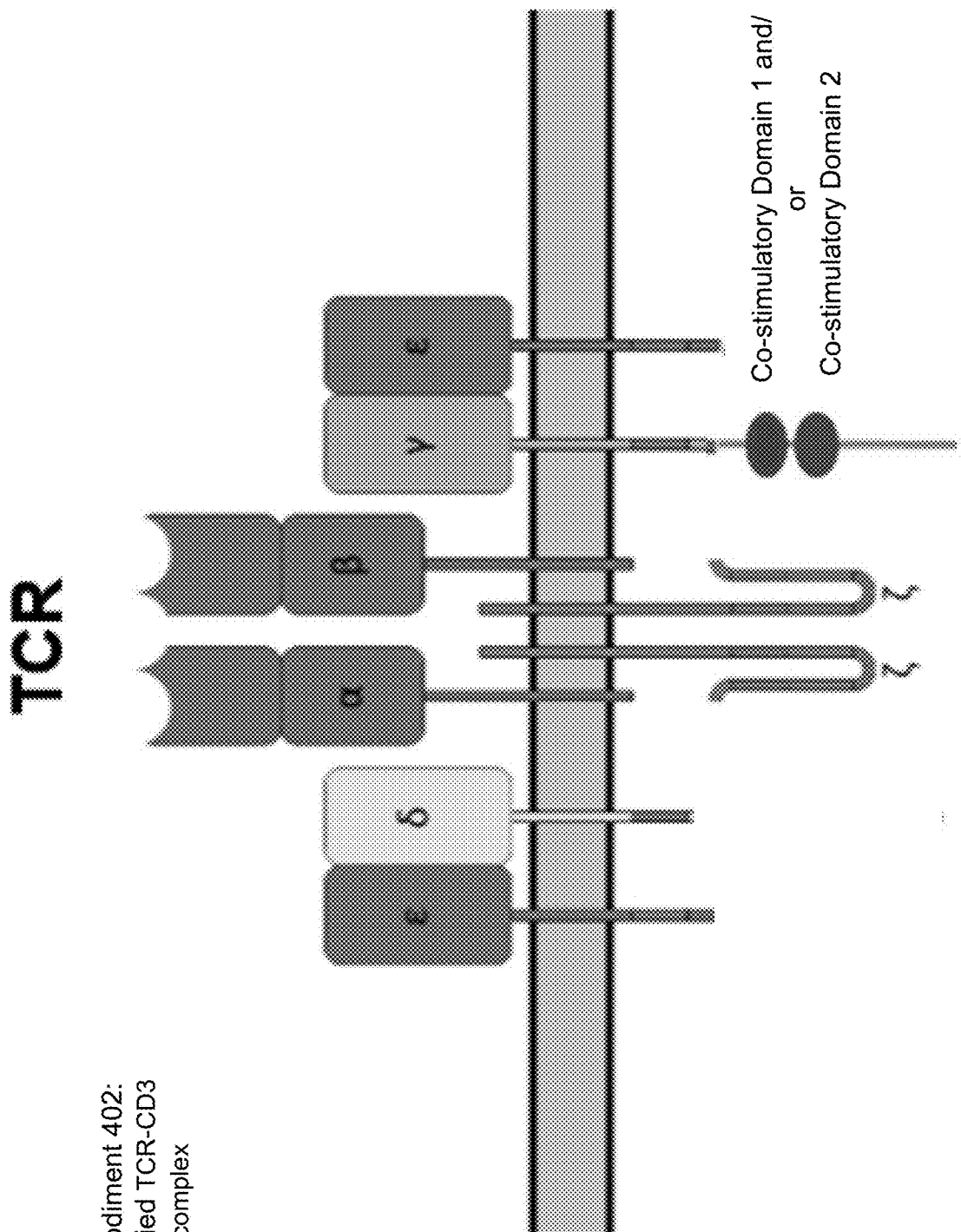
Figure 5:
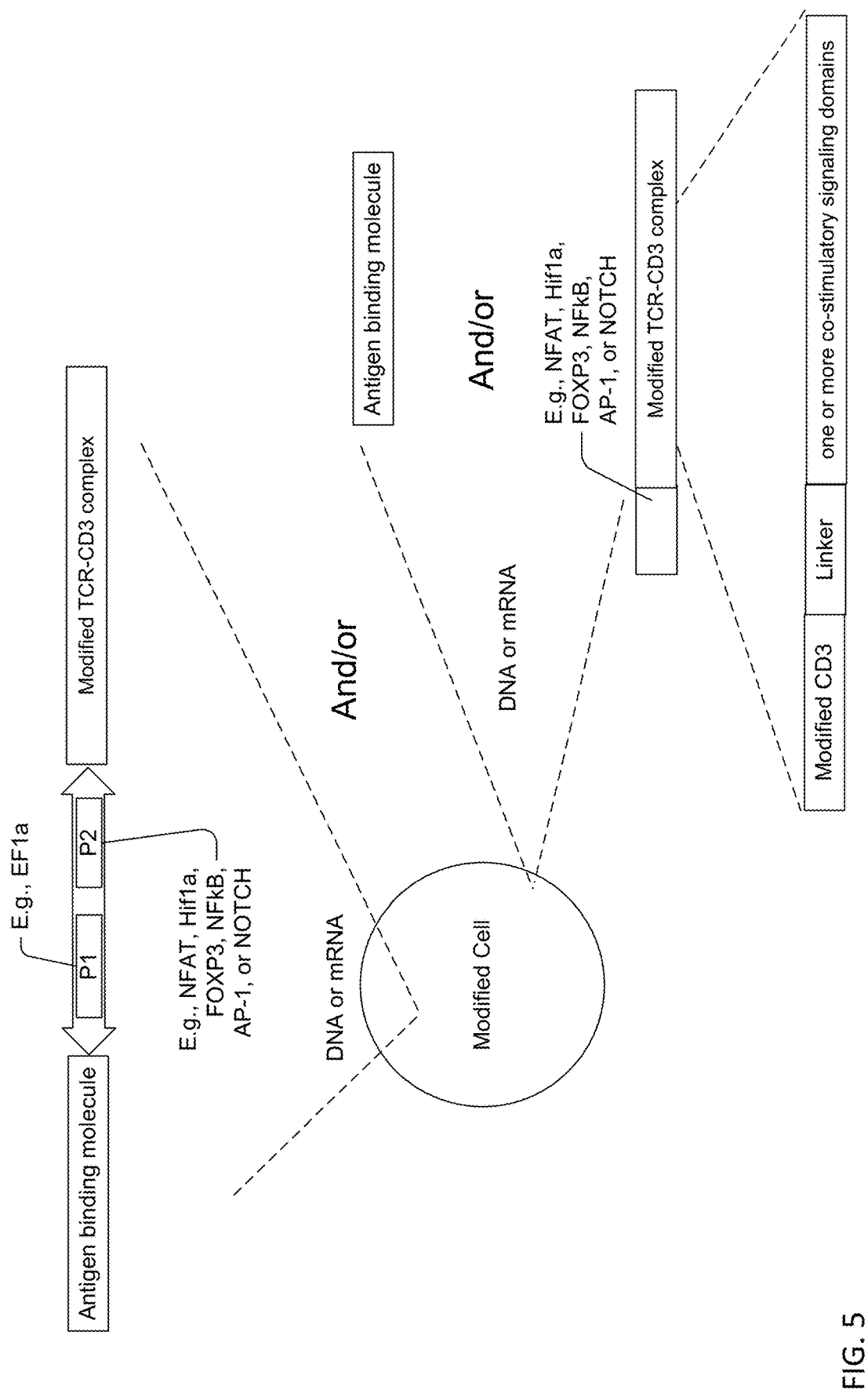
FIG. 5 shows a schematic diagram of polynucleotides and a modified cell.

Unless defined otherwise, all technical and scientific terms used herein have the same meaning as commonly understood by those of ordinary skill in the art to which the disclosure belongs. Although any method and material similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies; monoclonal antibodies; Fv, Fab, Fab', and F(ab')$_2$ fragments; as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragments" refers to a portion of a full-length antibody, for example, the antigen binding or variable region of the antibody. Other examples of antibody fragments include Fab, Fab', F(ab')$_2$, and Fv fragments; diabodies; linear antibodies; single-chain antibody molecules; and multi-specific antibodies formed from antibody fragments.

The term "Fv" refers to the minimum antibody fragment which contains a complete antigen-recognition and -binding site. This fragment consists of a dimer of one heavy- and one light-chain variable region domain in tight, non-covalent association. From the folding of these two domains emanates six hypervariable loops (3 loops each from the H and L chain) that contribute amino acid residues for antigen binding and confer antigen binding specificity to the antibody. However, even a single variable domain (or half of an Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and λ light chains refer to the two major antibody light chain isotypes.

The term "synthetic antibody" refers to an antibody which is generated using recombinant DNA technology, such as, for example, an antibody expressed by a bacteriophage. The term also includes an antibody which has been generated by the synthesis of a DNA molecule encoding the antibody and the expression of the DNA molecule to obtain the antibody or to obtain an amino acid encoding the antibody. The synthetic DNA is obtained using technology that is available and well known in the art.

The term "antigen" refers to a molecule that provokes an immune response, which may involve either antibody production, or the activation of specific immunologically-competent cells, or both. Antigens include any macromolecule, including all proteins or peptides, or molecules derived from recombinant or genomic DNA. For example, DNA including a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized or derived from a biological sample including a tissue sample, a tumor sample, a cell, or a biological fluid.

The term "anti-tumor effect" as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumor in the first place.

The term "auto-antigen" refers to an endogenous antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from a subject which is subsequently re-introduced into the same subject.

The term "allogeneic" is used to describe a graft derived from a different subject of the same species. As an example, a donor subject may be a related or unrelated to the recipient subject, but the donor subject has immune system markers which are similar to the recipient subject.

The term "xenogeneic" is used to describe a graft derived from a subject of a different species. As an example, the donor subject is from a different species than a recipient subject, and the donor subject and the recipient subject can be genetically and immunologically incompatible.

The term "cancer" is used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes" and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any element listed after the phrase and can include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements. For example, if the element does not affect the expansion, function, or the phenotype of the cells, then the element is not required and is considered optional.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules, or there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "co-stimulatory ligand," refers to a molecule on an antigen presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX4OL, inducible co-stimulatory ligand (ICOS-L), intercellular adhesion molecule (ICAM), CD3OL, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor, and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T cell proliferation and/or upregulation or downregulation of key molecules.

The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as a template for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression or overexpression" refers to the transcription and/or translation of a particular nucleotide sequence into a precursor or mature protein, for example, driven by its promoter. "Overexpression" refers to the production of a gene product in transgenic organisms or cells that exceeds levels of production in normal or non-transformed organisms or cells. As defined herein, the term "expression" refers to expression or overexpression.

The term "expression vector" refers to a vector including a recombinant polynucleotide including expression control (regulatory) sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Viruses can be used to deliver nucleic acids into a cell in vitro and in vivo (in a subject). Examples of viruses useful for delivery of nucleic acids into cells include retrovirus, adenovirus, herpes simplex virus, vaccinia virus, and adeno-associated virus.

There also exist non-viral methods for delivering nucleic acids into a cell, for example, electroporation, gene gun, sonoporation, magnetofection, and the use of oligonucleotides, lipoplexes, dendrimers, and inorganic nanoparticles.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous, then the two sequences are 60% homologous. By way of example, the DNA sequences ATTGCC and TATGGC share 50% homology. A comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

The term "substantially purified" refers to a material that is substantially free from components that are normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. Moreover, the use of lentiviruses enables integration of the genetic information into the host chromosome resulting in stably transduced genetic information. HIV, SIV, and FIV are all examples of lentiviruses. Vectors derived from lentiviruses offer the means to achieve significant levels of gene transfer in vivo.

The term "modulating," refers to mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

The term "under transcriptional control" refers to a promoter being operably linked to and in the correct location and orientation in relation to a polynucleotide to control (regulate) the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having solid tumor or a hematological malignancy characterized by overexpression of the tumor antigen can be determined by standard assays known in the art.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, Melanoma, and CNS tumors (such as a glioma (such as brainstem glioma and mixed gliomas), glioblastoma (also known as glioblastoma multiforme), astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma, and brain metastases).

A solid tumor antigen is an antigen expressed on a solid tumor. In embodiments, solid tumor antigens are also expressed at low levels on healthy tissue. Examples of solid tumor antigens and their related disease tumors are provided in Table 1.

TABLE 1

| Solid Tumor antigen | Disease tumor |
| --- | --- |
| PRLR | Breast Cancer |
| CLCA1 | colorectal Cancer |
| MUC12 | colorectal Cancer |
| GUCY2C | colorectal cancer and other digestive cancer types |
| GPR35 | colorectal Cancer |
| CR1L | Gastric Cancer |
| MUC 17 | Gastric Cancer |
| TMPRSS11B | esophageal Cancer |
| MUC21 | esophageal Cancer |
| TMPRSS11E | esophageal Cancer |
| CD207 | bladder Cancer |
| SLC30A8 | pancreatic Cancer |
| CFC1 | pancreatic Cancer |
| SLC12A3 | Cervical Cancer |
| SSTR1 | Cervical tumor |
| GPR27 | Ovary tumor |
| FZD10 | Ovary tumor |
| TSHR | Thyroid Tumor |
| SIGLEC15 | Urothelial cancer |
| SLC6A3 | Renal cancer |
| KISS1R | Renal cancer |
| QRFPR | Renal cancer: |
| GPR119 | Pancreatic cancer |
| CLDN6 | Endometrial cancer/ Urothelial cancer |
| UPK2 | Urothelial cancer (including bladder cancer) |
| ADAM12 | Breast cancer, pancreatic cancer and the like |

TABLE 1-continued

| Solid Tumor antigen | Disease tumor |
|---|---|
| SLC45A3 | Prostate cancer |
| ACPP | Prostate cancer |
| MUC21 | Esophageal cancer |
| MUC16 | Ovarian cancer |
| MS4A12 | Colorectal cancer |
| ALPP | Endometrial cancer |
| CEA | Colorectal carcinoma |
| EphA2 | Glioma |
| FAP | Mesotelioma |
| GPC3 | Lung squamous cell carcinoma |
| IL13-Rα2 | Glioma |
| Mesothelin | Metastatic cancer |
| PSMA | Prostate cancer |
| ROR1 | Breast lung carcinoma |
| VEGFR-II | Metastatic cancer |
| GD2 | Neuroblastoma |
| FR-α | Ovarian carcinoma |
| ErbB2 | Carcinomasb |
| EpCAM | Carcinomasa |
| EGFRvIII | Glioma-Glioblastoma |
| EGFR | Glioma-NSCL cancer |
| tMUC1 | Cholangiocarcinoma, Pancreatic cancer, Breast |
| PSCA | pancreas, stomach, or prostate cancer |
| FCER2, GPR18, FCRLA, CXCR5, FCRL3, FCRL2, HTR3A, and CLEC17A | breast cancer |
| TRPMI, SLC45A2, and SLC24A5 | Lymphoma |
| DPEP3 | Melanoma |
| KCNK16 | ovarian, testis |
| LIM2 or KCNV2 | Pancreatic |
| SLC26A4 | thyroid cancer |
| CD171 | Neuroblastoma |
| Glypican-3 | Sarcoma |
| IL-13 | Glioma |
| CD79a/b | Lymphoma |
| MAGE A4 | Lung cancer and multiple cancer types |

The term "parenteral administration" of a composition includes, e.g., subcutaneous (s.c.), intravenous (i.v.), intramuscular (i.m.), intrasternal injection, or infusion techniques.

The terms "patient," "subject," and "individual," and the like are used interchangeably herein and refer to any human, or animal, amenable to the methods described herein. In certain non-limiting embodiments, the patient, subject, or individual is a human or animal. In embodiments, the term "subject" is intended to include living organisms in which an immune response can be elicited (e.g., mammals). Examples of subjects include humans, and animals, such as dogs, cats, mice, rats, and transgenic species thereof.

A subject in need of treatment or in need thereof includes a subject having a disease, condition, or disorder that needs to be treated. A subject in need thereof also includes a subject that needs treatment for prevention of a disease, condition, or disorder.

The term "polynucleotide" or "nucleic acid" refers to mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes all forms of nucleic acids including single and double-stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In embodiments, a polypeptide variant is distinguished from a reference polypeptide by one or more substitutions, which may be conservative or non-conservative. In embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted or replaced with different amino acid residues.

The term "promoter" refers to a DNA sequence recognized by the synthetic machinery of the cell or introduced synthetic machinery, required to initiate the specific transcription of a polynucleotide sequence. The term "expression control (regulatory) sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a second molecule in a sample or organism but does not substantially recognize or adhere to other structurally unrelated molecules in the sample. The term "specifically binds," as used herein with respect to an antibody, refers to an antibody which recognizes a specific antigen, but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "K" and the antibody, will reduce the amount of labeled A bound to the antibody.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation," refers to a primary response induced by binding of a stimulatory molecule (e.g., a TCR/CD3 complex) with its cognate ligand thereby mediating a signal transduction event, such as signal transduction via the TCR/CD3 complex. Stimulation can mediate altered expression of certain molecules, such as downregulation of TGF-β, and/or reorganization of cytoskeletal structures.

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex. The stimulatory molecule includes a domain responsible for signal transduction.

The term "stimulatory ligand" refers to a ligand that when present on an antigen presenting cell (e.g., an APC, a dendritic cell, a B-cell, and the like.) can specifically bind with a cognate binding partner (referred to herein as a "stimulatory molecule") on a cell, for example a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to a treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease and its severity and the age, weight, etc., of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell is one which has been transfected, transformed, or transduced with exogenous nucleic acid. The cell includes the primary subject cell and its progeny.

The term "vector" refers to a polynucleotide that comprises an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate the transfer of nucleic acid into cells, such as, for example, polylysine compounds, liposomes, and the like. Examples of viral vectors include adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

A "chimeric antigen receptor" (CAR) molecule is a recombinant polypeptide including at least an extracellular domain, a transmembrane domain and a cytoplasmic domain or intracellular domain. In embodiments, the domains of the CAR are on the same polypeptide chain, for example a chimeric fusion protein. In embodiments, the domains are on different polypeptide chains, for example the domains are not contiguous.

The extracellular domain of a CAR molecule includes an antigen binding domain. The antigen binding domain is for expanding and/or maintaining the modified cells, such as a CAR T cell or for killing a tumor cell, such as a solid tumor. In embodiments, the antigen binding domain for expanding and/or maintaining modified cells binds an antigen, for example, a cell surface molecule or marker, on the surface of a WBC. In embodiments, the WBC is at least one of GMP (granulocyte macrophage precursor), MDP (monocyte-macrophage/dendritic cell precursors), cMoP (common monocyte precursor), basophil, eosinophil, neutrophil, SatM (Segerate-nucleus-containing atypical monocyte), macrophage, monocyte, CDP (common dendritic cell precursor), cDC (conventional D.C.), pDC (plasmacytoid D.C.), CLP (common lymphocyte precursor), B cell, ILC (Innate Lymphocyte), Natural Killer (NK) cell, megakaryocyte, myeloblast, pro-myelocyte, myelocyte, meta-myelocyte, band cells, lymphoblast, prolymphocyte, monoblast, megakaryoblast, promegakaryocyte, megakaryocyte, platelets, or MSDC (Myeloid-derived suppressor cell). In embodiments, the WBC is a granulocyte, monocyte and or lymphocyte. In embodiments, the WBC is a lymphocyte, for example, a B cell. In embodiments, the WBC is a B cell. In embodiments, the cell surface molecule of a B cell includes CD19, CD22, CD20, BCMA, CD5, CD7, CD2, CD16, CD56, CD30, CD14, CD68, CD11 b, CD18, CD169, CD1c, CD33, CD38, CD138, or CD13. In embodiments, the cell surface molecule of the B cell is CD19, CD20, CD22, or BCMA. In embodiments, the cell surface molecule of the B cell is CD19.

The cells described herein, including modified cells such as CAR cells and modified T cells can be derived from stem cells. Stem cells may be adult stem cells, embryonic stem cells, more particularly non-human stem cells, cord blood stem cells, progenitor cells, bone marrow stem cells, induced pluripotent stem cells, totipotent stem cells or hematopoietic stem cells. A modified cell may also be a dendritic cell, a NK-cell, a B-cell or a T cell selected from the group consisting of inflammatory T-lymphocytes, cytotoxic T-lymphocytes, regulatory T lymphocytes or helper T-lymphocytes. In embodiments, Modified cells may be derived from the group consisting of CD4+ T lymphocytes and CD8+ T lymphocytes. Prior to expansion and genetic modification of the cells, a source of cells may be obtained from a subject through a variety of non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In embodiments, any number of T cell lines available and known to those skilled in the art, may be used. In embodiments, modified cells may be derived from a healthy donor, from a patient diagnosed with cancer or from a patient diagnosed with an infection. In embodiments, a modified cell is part of a mixed population of cells which present different phenotypic characteristics.

A population of cells refers to a group of two or more cells. The cells of the population could be the same, such that the population is a homogenous population of cells. The cells of the population could be different, such that the population is a mixed population or a heterogeneous population of cells. For example, a mixed population of cells could include modified cells comprising a first CAR and cells comprising a second CAR, wherein the first CAR and the second CAR bind different antigens.

The term "stem cell" refers to any of certain types of cell which have the capacity for self-renewal and the ability to differentiate into other kind(s) of cell. For example, a stem cell gives rise either to two daughter stem cells (as occurs in vitro with embryonic stem cells in culture) or to one stem cell and a cell that undergoes differentiation (as occurs e.g. in hematopoietic stem cells, which give rise to blood cells). Different categories of stem cells may be distinguished on the basis of their origin and/or on the extent of their capacity for differentiation into other types of cell. For example, stem cells may include embryonic stem (E.S.) cells (i.e., pluripotent stem cells), somatic stem cells, induced pluripotent stem cells, and any other types of stem cells.

The pluripotent embryonic stem cells are found in the inner cell mass of a blastocyst and have an innate capacity for differentiation. For example, pluripotent embryonic stem cells have the potential to form any type of cell in the body. When grown in vitro for long periods of time, E.S. cells maintain pluripotency as progeny cells retain the potential for multilineage differentiation.

Somatic stem cells can include fetal stem cells (from the fetus) and adult stem cells (found in various tissues, such as bone marrow). These cells have been regarded as having a capacity for differentiation that is lower than that of the pluripotent E.S. cells—with the capacity of fetal stem cells being greater than that of adult stem cells. Somatic stem cells apparently differentiate into only a limited number of types of cells and have been described as multipotent. The "tissue-specific" stem cells normally give rise to only one type of cell. For example, embryonic stem cells may be differentiated into blood stem cells (e.g., Hematopoietic stem cells (HSCs)), which may be further differentiated into various blood cells (e.g., red blood cells, platelets, white blood cells, etc.).

Induced pluripotent stem cells (i.e., iPS cells or iPSCs) may include a type of pluripotent stem cell artificially derived from a non-pluripotent cell (e.g., an adult somatic cell) by inducing an expression of specific genes. Induced pluripotent stem cells are similar to natural pluripotent stem cells, such as embryonic stem (E.S.) cells, in many aspects, such as the expression of certain stem cell genes and proteins, chromatin methylation patterns, doubling time, embryoid body formation, teratoma formation, viable chimera formation, and potency and differentiability. Induced pluripotent cells can be obtained from adult stomach, liver, skin, and blood cells.

In embodiments, the antigen binding domain for killing a tumor, binds an antigen on the surface of a tumor, for example a tumor antigen or tumor marker. Tumor antigens are proteins that are produced by tumor cells that elicit an immune response, particularly T cell mediated immune responses. Tumor antigens are well known in the art and include, for example, tumor associated MUC1 (tMUC1), a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, surviving, telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, CD19, and mesothelin. For example, when the tumor antigen is CD19, the CAR thereof can be referred to as CD19 CAR (19CAR, CD19CAR, or CD19-CAR) which is a CAR molecule that includes an antigen binding domain that binds CD19.

In embodiments, the extracellular antigen binding domain of a CAR includes at least one scFv or at least a single domain antibody. As an example, there can be two scFvs on a CAR. The scFv includes a light chain variable (V.L.) region and a heavy chain variable (V.H.) region of a target antigen-specific monoclonal antibody joined by a flexible linker. Single chain variable region fragments can be made by linking light and/or heavy chain variable regions by using a short linking peptide (Bird et al., Science 242:423-426, 1988). An example of a linking peptide is the G.S. linker having the amino acid sequence (GGGGS)$_3$ (SEQ ID NO: 118), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. The single chain variants can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect, or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The cytoplasmic domain of the CAR molecules described herein includes one or more co-stimulatory domains and one or more signaling domains. The co-stimulatory and signaling domains function to transmit the signal and activate molecules, such as T cells, in response to antigen binding. The one or more co-stimulatory domains are derived from stimulatory molecules and/or co-stimulatory molecules, and the signaling domain is derived from a primary signaling domain, such as the CD3 zeta domain. In embodiments, the signaling domain further includes one or more functional signaling domains derived from a co-stimulatory molecule. In embodiments, the co-stimulatory molecules are cell surface molecules (other than antigens receptors or their ligands) that are required for activating a cellular response to an antigen.

In embodiments, the co-stimulatory domain includes the intracellular domain of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, or any combination thereof. In embodiments, the signaling domain includes a CD3 zeta domain derived from a T cell receptor.

The CAR molecules described herein also include a transmembrane domain. The incorporation of a transmembrane domain in the CAR molecules stabilizes the molecule. In embodiments, the transmembrane domain of the CAR molecules is the transmembrane domain of a CD28 or 4-1BB molecule.

Between the extracellular domain and the transmembrane domain of the CAR, there may be incorporated a spacer domain. As used herein, the term "spacer domain" generally means any oligo- or polypeptide that functions to link the transmembrane domain to the extracellular domain and/or the cytoplasmic domain on the polypeptide chain. A spacer domain may include up to 300 amino acids, preferably 10 to 100 amino acids, and most preferably 25 to 50 amino acids.

Embodiments relate to a polynucleotide encoding a modified component of the TCR-CD3 complex. Embodiments relate to a vector comprising the polynucleotide. Embodiments relate to a cell modified comprising the polynucleotide. Embodiments relate to a modified cell engineered to express a modified component of the TCR-CD3 complex, wherein the modified cell includes an antigen binding molecule. Embodiments relate to a method or use of polynucleotide, the method comprising providing a viral particle (e.g., AAV, lentivirus or their variants) comprising a vector genome, the vector genome comprising the polynucleotide; and administering an amount of the viral particle to a subject such that the polynucleotide is expressed in the subject. In embodiments, the AAV preparation may include AAV vector particles, empty capsids, and host cell impurities, thereby providing an AAV product substantially free of AAV empty capsids. Embodiments relate to a pharmaceutical composition comprising the population of the cells. Embodiments relate to a method of causing or eliciting T cell response in a subject in need thereof and/or treating a tumor of the subject, the method comprising administering an effective amount of the composition. In embodiments, the polynucleotide comprises at least one of the sequences listed in Table 2. For example, the antigen-specific T cell receptor (TCR) is composed of a disulfide-linked heterodimer, containing two clonally distributed, integral membrane glycoprotein chains, α, and β, or γ and δ non-covalently associated with a complex of low molecular weight invariant proteins, commonly designated as CD3 (i.e., TCR-CD3 complex). The TCR α and β chains determine antigen specificities, and the CD3 structures are thought to represent accessory molecules that may be the transducing elements of activation signals initiated upon binding of the TCR αβ to its ligand. TCR complex interacts with small peptidic antigen presented in the context of major histocompatibility complex (MHC) proteins. The MHC proteins represent another highly polymorphic set of molecules randomly dispersed throughout the species.

The modified components of the TCR-CD3 complex can be expressed in TIL or TCR T as a whole and can replace the peptide chain in CD3 so that when CD3 is activated, there will be a signal of a co-stimulatory domain and enhance TIL/TCR-T. Ordinary TCR only activates CD3, the designed TCR-CD3 complex here has been added with a co-stimulation domain, and the signal is stronger. The designed TCR-CD3 complex may be associated with the uses of a CAR and can be a general-purpose component. And when CD3 is activated, there will be a co-stimulus domain signal, which can enhance the killing effect of TCR-T. In embodiments, the TCR-CD3 complex comprises TCRα, TCRβ, CD3γ, ζ-chain, CD3ε, and CD3δ. In embodiments, the TCR-CD3 complex comprises TCRγ, TCRδ, CD3γ, ζ-chain, CD3ε, and CD3δ. In embodiments, the modified component of the TCR-CD3 complex comprises components of TCR-CD3 complex linked to one or more co-stimulatory signaling domains.

In embodiments, the one or more co-stimulatory signaling domains comprise one or more functional signaling domains of one or more proteins selected from the group consisting of CD27, CD28, 4-1BB(CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM(LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, vFLIP K13, K13-opt, a NEMO mutant, a NEMO-fusion protein, IKKI-S176E-S180E, IKK2-S177E-S181E, RIP, IKKα, IKKβ, Tcl-I, MyD88-L265,ally NF-KB actuating protein or protein fragment. any inhibitor of an inhibiior of NF-kB, pathway, any gene editing sysiem capable of selectively activating NF-κB.

In embodiments, the one or more co-stimulatory signaling domains comprise one or more functional signaling domains of one or more proteins selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In embodiments, the modified component of the TCR-CD3 complex comprises CD3γ, ζ-chain, CD3ε, and/or CD3δ. In embodiments, the modified component of the TCR-CD3 complex comprises CD3γ linked to one or more co-stimulatory signaling domains. In embodiments, the modified component of the TCR-CD3 complex comprises CD3ζ linked to one or more co-stimulatory signaling domains. In embodiments, the modified component of the TCR-CD3 complex comprises CD3ε linked to one or more co-stimulatory signaling domains. In embodiments, the modified component of the TCR-CD3 complex comprises CD3δ linked to one or more co-stimulatory signaling domains. In embodiments, the CD3γ, ζ-chain, CD3ε, and/or CD3δ and the one or more co-stimulatory signaling domains are linked by a linker (e.g., G.S. linker). In embodiments, the one or more co-stimulatory signaling domains comprise at least two co-stimulatory signaling domains. In embodiments, at least two co-stimulatory signaling domains are linked by a linker (e.g., G.S. linker). In embodiments, the modified component of the TCR-CD3 complex is the modified CD3 domain. In embodiments, the modified TCR-CD3 complex is overexpressed by the modified cell, and/or the modified CD3 domain is overexpressed by the modified cell.

In embodiments, the expression of the modified component of the TCR-CD3 complex may be regulated by an inducible expression system. The inducible expression system allows for a temporal and spatial controlled activation and/or expression of genes. For example, Tetracycline-Controlled Transcriptional Activation is a method of inducible gene expression where transcription is reversibly turned on or off in the presence of the antibiotic tetracycline or one of its derivatives (e.g., doxycycline). For example, an inducible suicide gene expression system allows for a temporal and spatial controlled activation and/or expression of a suicide gene, which causes a cell to kill itself through apoptosis.

In embodiments, the modified cells comprise a nucleic acid sequence encoding a reverse tetracycline transactivator (rtTA). In embodiments, the expression of one or more molecules is regulated by the rtTA, such that the modified component of the TCR-CD3 complex is expressed in the presence of tetracycline. In embodiments, a concentration of tetracycline in the cell culture medium is not less than about 2 μg/ml. In embodiments, the tetracycline is selected from the group consisting of tetracycline, demeclocycline, meclo-cycline, doxycycline, lymecycline, methacycline, minocycline, oxytetracycline, rolitetracycline, and chlortetracycline. In embodiments, the tetracycline is doxycycline.

In embodiments, the inducible suicide system is an HSV-TK system or an inducible caspase-9 system. In embodiments, the modified cells comprise a nucleic acid sequence encoding a suicide gene, such that when the modified cells are in the presence of a nucleoside analogue in a manner permitting expression of the suicide gene, to render the nucleoside analogue cytotoxic to the modified cells. In embodiments, the suicide gene is selected from the group consisting of thymidine kinase of herpes simplex virus, thymidine kinase of varicella zoster virus, and bacterial cytosine deaminase. In embodiments, the suicide gene is thymidine kinase of herpes simplex virus. In embodiments, the nucleoside analogue is selected from the group consisting of ganciclovir, acyclovir, buciclovir, famciclovir, penciclovir, valciclovir, trifluorothymidine, 1-[2-deoxy, 2-fluoro, beta-D-arabino furanosyl]-5-iodouracil, ara-A, araT 1-beta-D-arabinofuranoxyl thymine, 5-ethyl-2'-deoxyuridine, 5-iodo-5'-amino-2,5'-dideoxpridine, idoxuridine, AZT, AIU, dideoxycytidine, and AraC. In embodiments, the nucleoside analogue is ganciclovir.

In embodiments, the expression of the modified component of the TCR-CD3 complex is regulated by one or more promoters. In embodiments, the polynucleotide comprises a promoter comprising a binding site for a transcription modulator that modulates the expression and/or secretion of the modified component of the TCR-CD3 complex in the cell. For example, the transcription modulator is or includes Hif1a, NFAT, FOXP3, and/or NFkB. For example, the modified component of the TCR-CD3 complex comprises at least one co-stimulatory signaling domain associated with an oxygen-sensitive polypeptide domain, and the oxygen-sensitive polypeptide domain comprises HIF VHL binding domain.

In embodiments, the polynucleotide may integrate into the genome of the modified cell, and descendants of the modified cell will also express the polynucleotide, resulting in a stably transfected modified cell. In embodiments, the modified cell may express the polynucleotide encoding the CAR, but the polynucleotide does not integrate into the genome of the modified cell such that the modified cell expresses the transiently transfected polynucleotide for a finite period of time (e.g., several days), after which the polynucleotide is lost through cell division or other factors. For example, the polynucleotide is present in the modified cell in a recombinant DNA construct, in an mRNA, or in a viral vector, and/or the polynucleotide is an mRNA, which is not integrated into the genome of the modified cell.

Embodiments related to a method or use of polynucleotide, the method comprising providing a viral particle (e.g., AAV, lentivirus or their variants) comprising a vector genome, the vector genome comprising the polynucleotide encoding the one more molecules and a polynucleotide encoding a binding molecule, the polynucleotide operably linked to an expression control element conferring transcription of the polynucleotides; and administering an amount of the viral particle to a subject such that the polynucleotide is expressed in the subject. In embodiments, the AAV preparation may include AAV vector particles, empty capsids, and host cell impurities, thereby providing an AAV product substantially free of AAV empty capsids.

Embodiments relate to a method or use of polynucleotide. The method or use includes: providing a viral particle (e.g., AAV, lentivirus or their variants) comprising a vector genome, the vector genome comprising the polynucleotide, wherein the polynucleotide is operably linked to an expression control element conferring transcription of the polynucleotide, and administering an amount of the viral particle to the subject such that the polynucleotide is expressed in the subject. In embodiments, the AAV preparation may include AAV vector particles, empty capsids, and host cell impurities, thereby providing an AAV product substantially free of AAV empty capsids. More information of the administration and preparation of the viral particle may be found at the U.S. Pat. No. 9,840,719 and Milani et al., Sci. Transl. Med. 11, eaav7325 (2019) May 22, 2019, which are incorporated herein by reference.

In embodiments, the bioreactor may be inoculated at a cell density of approximately $0.5 \times 10^6$ cells/mL with viability greater than 95%. When the cell density reaches approximately $1.0 \times 10^6$ cells/ml, the cells may be transfected with the PEI/DNA complexes (polyplexes) with a PEI to DNA ratio of 2:1. At the time of harvest, AAV from the cell culture in the bioreactor may be released using the Triton X-100 method. All solutions may be added directly to the bioreactor, and the lysate was centrifuged at 4000×g for 20 min. The supernatant may be stored at −80° C. for further processing. AAV may be further purified. For example, AAV samples (12.3 mL) may be purified by overlaying them on top of series of step gradients using 15, 25, 40, and 54% iodixanol concentrations containing 1, 5, 7, and 5 mL, respectively. The 15% iodixanol concentration also contains 1 M NaCl to avoid aggregation of AAV with other cellular proteins and negatively charged nuclear components. After the completion of centrifugation, 5 mL may be withdrawn from 2 mm below the 40/54 interface marked before starting the ultracentrifugation at 385,000×g for 1 h 45 min in Sorvals T-865 rotor in Sorval Ultracentrifuge. The viral vectors may then be quantified. For example, vectors AAV infectivity may be determined by the gene transfer assay (GTA) using GFP as a reporter gene in all cases. AAV infectivity assay where the sample may be diluted before addition to the cells to have the GFP positive cells in the range of 2-20% to assure that only a single virus has entered the cell for GFP expression. The GFP-positive cells may be quantified by FACS using HEK293 cells in suspension. The AAV may be then administered to a subject. For example, AAV may be diluted in 0.9% sterile NaCl saline solution (supplemented with 0.25% human serum albumin [HSA]) for infusion in patients, and the final volume of infusion will be calculated based on the patient's weight as 3 mL/kg.

In embodiments, the modified cell comprises the antigen binding molecule, the antigen binding molecule is chimeric antigen receptor (CAR), which comprises an antigen-binding domain, a transmembrane domain, and an intracellular signaling domain. In embodiments, the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LACE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1. In embodiments, the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D In embodiments, the modified cell comprises the antigen binding molecule, the antigen binding molecule is a modified TCR. In embodiments, the TCR is derived from spontaneously occurring tumor-specific T cells in patients. In embodiments, the TCR binds to a tumor antigen. In embodiments, the tumor antigen comprises CEA, gp100, MART-1, p53, MAGE-A3, or NY-ESO-1. In embodiments, the TCR comprises TCRγ and TCRδ Chains or TCRα and TCRβ chains, or a combination thereof.

In embodiments, the first antigen binding domain is on a CAR, and the second antigen binding domain is on a T Cell Receptor (TCR). In embodiments, the TCR is a modified TCR. In embodiments, the TCR is derived from spontaneously occurring tumor-specific T cells in patients. In embodiments, the TCR binds a tumor antigen. In embodiments, the tumor antigen comprises CEA, gp100, MART-1, p53, MAGE-A3, or NY-ESO-1.

In embodiments, a T cell clone that expresses a TCR with a high affinity for the target antigen may be isolated. Tumor-infiltrating lymphocytes (TILs) or peripheral blood mononuclear cells (PBMCs) can be cultured in the presence of antigen-presenting cells (APCs) pulsed with a peptide representing an epitope known to elicit a dominant T cell response when presented in the context of a defined HLA allele. High-affinity clones may be then selected on the basis of MHC-peptide tetramer staining and/or the ability to recognize and lyse target cells pulsed with low titrated concentrations of cognate peptide antigen. After the clone has been selected, the TCRα and TCRβ chains or TCRγ and TCRδ chains are identified and isolated by molecular cloning. For example, for TCRα and TCRβ chains, the TCRα and TCRβ gene sequences are then used to generate an expression construct that ideally promotes stable, high-level expression of both TCR chains in human T cells. The transduction vehicle, for example, a gammaretrovirus or lentivirus, can then be generated and tested for functionality (antigen specificity and functional avidity) and used to produce a clinical lot of the vector. An aliquot of the final product can then be used to transduce the target T cell population (generally purified from patient PBMCs), which is expanded before infusion into the patient.

Various methods may be implemented to obtain genes encoding tumor-reactive TCR. More information is provided in Kershaw et al., Clin Transl Immunology. 2014 May; 3(5): e16. In embodiments, specific TCR can be derived from spontaneously occurring tumor-specific T cells in patients. Antigens included in this category include the melanocyte differentiation antigens MART-1 and gp100, as well as the MAGE antigens and NY-ESO-1, with expression in a broader range of cancers. TCRs specific for viral-associated malignancies can also be isolated, as long as viral proteins are expressed by transformed cells. Malignancies in this category include liver and cervical cancer, associated with hepatitis and papilloma viruses, and Epstein-Barr virus-associated malignancies. In embodiments, target antigens of the TCR may include CEA (e.g., for colorectal cancer), gp100, MART-1, p53 (e.g., for Melanoma), MAGE-A3 (e.g., Melanoma, esophageal and synovial sarcoma), NY-ESO-1 (e.g., for Melanoma and sarcoma as well as Multiple myelomas).

In embodiments, preparation and transfusion of tumor-infiltrating lymphocytes (TIL) may be implemented by the following. For example, tumor tissue comes from surgical or biopsy specimens, may be obtained under aseptic conditions, and transported to the cell culture chamber in an icebox. Necrotic tissue and adipose tissue may be removed. The tumor tissue may be cut into small pieces of about 1-3 cubic millimeters. Collagenase, hyaluronidase, and DNA enzyme may be added and digested overnight at 4° C. Filtering with 0.2 um filter, cells may be separated and collected by lymphocyte separation fluid, 1500 rpm for 5 min. Expanding the cells with a culture medium comprising PHA, 2-mercaptoethanol, and a CD3 monoclonal antibody, a small dose of IL-2 (10-20 IU/ml) may be added to induce activation and proliferation. According to the growth situation, the cell density may be carefully detected and maintained within the range of $0.5-2\times10^6$/ml under the condition of 37° C. and 5% CO2 for 7-14 days. TIL positive cells have the ability to kill homologous cancer cell may be screened out by co-culture. The positive cells may be amplified in a serum-free medium containing a high dose of IL2 (5000-6000 IU/ml) until greater than $1\times10^{11}$ TILs may be obtained. To administer TILs, they may be first collected in saline using continuous-flow centrifugation and then filtered through a platelet-administration set into a volume of 200-300 ml containing 5% albumin and 450 000 IU of IL-2. The TILs may be infused into patients through a central venous catheter over a period of 30-60 minutes. In embodiments, TILs may be often infused in two to four separate bags; the infusions may be separated by several hours. If more than approximately $1.5\times10^{11}$ TILs may be administered, they may be generally given on 2 successive days.

In embodiments, the cell is an immune effector cell (e.g., a population of immune effector cells). In embodiments, the immune effector cell is a T cell or an NK Cell. In embodiments, the immune effector cell is a T cell. In embodiments, the T cell is a CD4+ T cell, a CD8+ T cell, or a combination thereof. In embodiments, the cell is a human cell.

In embodiments, the enhanced expression and/or function of the modified component of TCR-CD3 complex is implemented by introducing a nucleic acid sequence encoding the modified component of TCR-CD3 complex and/or the binding molecule, which is present in the modified cell in a recombinant DNA construct, in an mRNA, or in a viral vector.

In embodiments, the nucleic acid sequence is an mRNA, which is not integrated into the genome of the modified cell. In embodiments, the nucleic acid sequence is associated with an oxygen-sensitive polypeptide domain. In embodiments, the oxygen-sensitive polypeptide domain comprises HIF VHL binding domain. In embodiments, the nucleic acid sequence is regulated by a promoter comprising a binding site for a transcription modulator that modulates the expression and/or secretion of the therapeutic agent in the cell. In embodiments, the transcription modulator is or includes Hif1a, NFAT, FOXP3, and/or NFkB.

Embodiments relate to compositions and methods for enhancing modified cells (e.g., immune cells) metabolism in the tumor microenvironment. For example, the metabolism of lactic acid (e.g, transporters MCT1, and MCT4) may be enhanced for lactic acid metabolism. Anaerobic and aerobic respiration and mitochondrial function and/or the metabolism of amino acids may be enhanced. The modified cells have enhanced metabolism by enhancing the pathway of metabolizing lactic acid (e.g., uses of transporters MCT1, MCT4 to enhance lactic acid metabolism) (e.g., molecules listed in Table 7), anaerobic and aerobic respiration mitochondrial function (e.g., molecules listed in Table 8), and/or the metabolism of amino acids (e.g., molecules listed in Table 9).

Conditions of the tumor microenvironment (such as hypoxia, high acid, etc.) inhibit T cell viability, and enhancing the function of T cell monocarboxylate transporter can effectively help T cells survive in the tumor microenvironment. MCT1 is normally expressed on T cells, regulates the two-way transport of lactic acid inward and outward, and is also expressed in tumor cells. MCT4 is highly expressed in some tumor cells, regulates the outward transport of lactic acid, and does not express on normal T cells. MCT2 is expressed on normal T cells and is expressed on some other cells in the body, regulating the transport of lactic acid into cells. CD147 is an accessory protein of MCT family proteins, which regulates the correct localization of MCT family proteins on the cell membrane. LDHB converts lactic acid to pyruvate. Pyruvate can enter the mitochondria through the pyruvate transporter (MPC) on the mitochondrial membrane and eventually oxidize and decompose through mitochondria. By knockdown/out MCT1/2, overexpression of MCT3 allows lactic acid not to enter T cells. By overexpressing MCT1/2, knockdown/out MCT3, and over-expressing LDHB and MPC, it can enhance the entry of lactic acid into T cells and enhance the metabolism of lactic acid, helping immune cells to enhance their effects in the face of solid tumors. The oxidative function of mitochondria may be implemented by overexpressing mitochondrial proteins such as Frataxin, HBA, HBB, HBD, HBE, and/or HBG, etc., it promotes the synthesis of heme and hemoglobin and enhances the mitochondrial oxygen storage capacity; By over-expressing TOMM20, TOMM22, TOMM40, and/or TOM70 to promote the assembly of mitochondria, the function of mitochondria is finally enhanced, and the immune cells are adapted to the tumor microenvironment, and the tumor treatment ability is increased. In order to make T cells more amino acids can be used: Overexpression of amino acid transporters CD98, SNAT1, SNAT2, and/or ASCT2, etc., transport amino acids from the extracellular to intracellular, or can be converted to glutamine salt into the tricarboxylic acid cycle by GLS glutamine. It is then converted from POA to PEP by PCK enzyme.

Embodiments relate to a cell modified to express one or more molecules at a level that is higher or lower than the level of the one or more expressed by a cell that has not been modified to expression the one or more molecules, wherein the one or more molecules are associated with metabolism of the modified cell. Embodiments relate to a modified cell engineered to express an antigen binding molecule, wherein expression and/or function of one or more molecules in the modified cell has been enhanced or reduced (including eliminated), where the one or more molecules are associated with the metabolism of the modified cell. In some embodiments, the modified cell comprises a disruption in an endogenous gene or addition of exogenous gene that is associated with a biosynthesis or transportation pathway of the one or more molecules. Embodiments relate to a pharmaceutical composition comprising the population of the cells. Embodiments relate to a method of causing or eliciting T cell response in a subject in need thereof and/or treating a tumor of the subject, the method comprising administering an effective amount of the composition of claim 6 to the subject. Embodiments relate to an isolated nucleic acid sequence encoding one or more molecules are associated with metabolism of the modified cell.

Embodiments relate to a method or use of polynucleotide, the method comprising providing a viral particle (e.g., AAV, lentivirus or their variants) comprising a vector genome, the vector genome comprising the polynucleotide encoding the one more molecules and a polynucleotide encoding a binding molecule, the polynucleotide operably linked to an expression control element conferring transcription of the polynucleotides; and administering an amount of the viral particle to a subject such that the polynucleotide is expressed in the subject, where the one or more molecules are overexpressed in cancer cells, associated with recruitment of immune cells, and/or associated with autoimmunity. In embodiments, the AAV preparation may include AAV vector particles, empty capsids, and host cell impurities, thereby providing an AAV product substantially free of AAV empty capsids.

In embodiments, the one more molecules comprise at least one of MCT1, MCT2, MCT3, LDHB, and MPC, a functional variant of the one or more molecules, or a functional fragment of the one or more molecules; and/or the metabolism comprises metabolism of lactic acid.

In embodiments, the metabolism comprises the transportation of lactic acid of the modified cells, which is changed.

In embodiments, the modified cells transport less or more lactic acid into the modified cells than that of corresponding wild-type cells.

In embodiments, the modified cells overexpress MCT 3 and express less MCT1 and MCT2, and transport less lactic acid into the modified cells than that of corresponding wild-type cells.

In embodiments, the modified cells overexpress MCT1, MCT2, LDHB, and MPC, express less MCT3, and transport more lactic acid into the modified cells than that of corresponding wild-type cells.

In embodiments, the one more molecules comprise at least one of Frataxin, HBA, HBB, HBD, HBE, HBG, TOMM20, and TOMM22, a functional variant of the one or more molecules, or a functional fragment of the one or more molecules; and/or the metabolism comprises metabolism of lactic acid.

In embodiments, the metabolism comprises the oxidative function of mitochondria of the modified cells, which is enhanced.

In embodiments, the modified cells overexpress Frataxin, HBA, HBB, HBD, HBE, HBG, such as to enhances the mitochondrial oxygen storage capacity of the modified cells.

In embodiments, the modified cells overexpress TOMM20 and TOMM22, such as to enhance functions of mitochondria of the modified cells.

In embodiments, the one more molecules comprise at least one of CD98, SNAT1, SNAT2, ASCT2, a functional variant of the one or more molecules, or a functional fragment of the one or more molecules; and/or the metabolism comprises metabolism of lactic acid.

In embodiments, the metabolism comprises the metabolism of amino acids of the modified cells, which is enhanced.

In embodiments, the modified cells overexpress CD98, SNAT1, SNAT2, ASCT2, such as to enhances the transportation capability for the modified cells to transport the amino acids into the modified cells.

Embodiments relate to a method of modifying a target genomic locus in a T cell to downregulate a gene of interest, the method comprising: introducing into the T cell a nuclease agent that makes a single or double-strand break within the target genomic locus; and introducing into the cell a nucleic acid insert such as to knock down or out the gene of interest; and selecting the cell comprising the nucleic acid insert integrated into the target genomic locus. In some embodiments, the nucleic acid insert is flanked by a 5' homology arm and a 3' homology arm, and the 3' homology arm of the nucleic acid insert and the 5' homology arm of the nucleic acid insert are homologous to corresponding genomic segments within the target genomic locus. In some embodiments, the nuclease agent is a zinc finger nuclease (ZFN), a Transcription Activator-Like Effector Nuclease (TALEN), or a meganuclease. In certain embodiments, the nuclease agent comprises a Clustered Regularly Interspaced Short Palindromic Repeats (CRISPR)-associated (Cas) protein and a guide RNA (gRNA). For example, the Cas protein is Cas9.

In embodiments, expression of the polynucleotide is regulated or modulated by a synthetic Notch receptor comprising, from N-terminal to C-terminal and in covalent linkage: a) an extracellular domain comprising an antibody (e.g., a single-chain Fv (scFv) or a nanobody) that specifically binds to an antigen; b) a Notch regulatory region (NRR) and c) an intracellular domain comprising a transcriptional activator comprising a DNA binding domain. In embodiments, the Notch regulatory region comprises a Lin 12-Notch repeat, a heterodimerization domain comprising an S2 proteolytic cleavage site, and a transmembrane domain comprising an S3 proteolytic cleavage site. The intracellular domain is heterologous to the Notch regulatory region. In some embodiments, the transcriptional activator replaces a naturally-occurring intracellular notch domain, and binding of the antibody to the antigen induces cleavage at the S2 and S3 proteolytic cleavage sites, thereby releasing the intracellular domain. The release of the intracellular domain causes the transcriptional activator to induce expression of the polynucleotide encoding one or more target proteins in the modified cell. In embodiments, the modified cell comprises a polynucleotide encoding the synthetic Notch receptor and a polynucleotide encoding a transcriptional control element that is responsive to the transcriptional activator and operably linked to the polynucleotide encoding one or more target proteins (e.g., overexpression of molecules related to metabolism described herein).

EXEMPLARY EMBODIMENTS

The following are exemplary embodiments:
1. A polynucleotide encoding a modified component of the TCR-CD3 complex.
2. A vector comprising the polynucleotide of embodiment 1.
2. A cell modified comprising the polynucleotide of embodiment 1.
3. A modified cell engineered to express a modified component of the TCR-CD3 complex, wherein the modified cell includes an antigen binding molecule.
4. A method or use of polynucleotide, the method comprising
   providing a viral particle (e.g., AAV, lentivirus or their variants) comprising a vector genome, the vector genome comprising the polynucleotide of embodiment 1; and
   administering an amount of the viral particle to a subject such that the polynucleotide is expressed in the subject.
5. The method of embodiment 4, wherein the AAV preparation may include AAV vector particles, empty capsids, and host cell impurities, thereby providing an AAV product substantially free of AAV empty capsids.
6. A pharmaceutical composition comprising the population of the cells of any of embodiments 2 and 3.
7. A method of causing or eliciting T cell response in a subject in need thereof and/or treating a tumor of the subject, the method comprising administering an effective amount of the composition of embodiment 6 to the subject.
8. The polynucleotide of any proceeding embodiments 1-7, wherein the polynucleotide comprises at least one of the sequences listed in Table 2.
9. The polynucleotide, vector, modified cell, and method of any of embodiments 1-8, wherein the TCR-CD3 complex comprises TCRα, TCRβ, CD3γ, ζ-chain, CD3ε, and CD3δ.
10. The polynucleotide, vector, modified cell, and method of any of embodiments 1-8, wherein the TCR-CD3 complex comprises TCRγ, TCRδ, CD3γ, ζ-chain, CD3ε, and CD3δ.
11. The polynucleotide, vector, modified cell, and method of any of embodiments 1-10, wherein the modified component of TCR-CD3 complex comprises components of TCR-CD3 complex linked to one or more co-stimulatory signaling domains.
12. The polynucleotide, vector, modified cell, and method of embodiment 11, wherein the one or more co-stimulatory signaling domains comprise one or more functional signaling domains of one or more proteins selected from the group consisting of CD27, CD28, 4-1BB(CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM(LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, vFLIP K13, K13-opt, a NEMO mutant, a NEMO-fusion protein, IKKI-S176E-S180E, IKK2-S177E-S181E, RIP, IKKα, IKKβ, Tcl-I, MyD88-L265,ally NF-KB actuating protein or protein fragment. any inhibitor of an inhibiior of NF-kB, pathway, any gene editing sysiem capable of selectively activating NF-κB. 13. The polynucleotide, vector, modified cell, and method of embodiment 11, wherein the one or more co-stimulatory signaling domains comprise one or more functional signaling domains of one or more proteins selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.
14. The polynucleotide, vector, modified cell, and method of any of embodiments 1-13, wherein the modified component of TCR-CD3 complex comprises CD3γ, ζ-chain, CD3ε, and/or CD3δ.
15. The polynucleotide, vector, modified cell, and method of any of embodiments 1-13, wherein the modified component of TCR-CD3 complex comprises CD3γ linked to one or more co-stimulatory signaling domains, and/or the modified component of TCR-CD3 complex comprises CD3ζ linked to one or more co-stimulatory signaling domains.
16. The polynucleotide, vector, modified cell, and method of any of embodiments 1-13, wherein the modified component of TCR-CD3 complex comprises CD3ε linked to one or more co-stimulatory signaling domains.
17. The polynucleotide, vector, modified cell, and method of any of embodiments 1-13, wherein the modified component of TCR-CD3 complex comprises CD3δ linked to one or more co-stimulatory signaling domains.
18. The polynucleotide, vector, modified cell, and method of any of embodiments 14-17, wherein the CD3γ, ζ-chain, CD3ε, and/or CD3δ and the one or more co-stimulatory signaling domains are linked by a linker (e.g., G.S. linker).
19. The polynucleotide, vector, modified cell, and method of any of embodiments 14-17, wherein the one or more co-stimulatory signaling domains comprise at least two co-stimulatory signaling domains.
20. The polynucleotide, vector, modified cell, and method of embodiment 19, wherein the at least two co-stimulatory signaling domains are linked by a linker (e.g., G.S. linker).
21. The modified cell of any proceeding embodiments 1-20, wherein the modified component of the TCR-CD3 complex is modified CD3 domain.
22. The modified cell of any proceeding embodiments 1-21, wherein the modified TCR-CD3 complex is overexpressed by the modified cell, and/or the modified CD3 domain is overexpressed by the modified cell.

23. The modified cell of any of the preceding embodiments, wherein the modified cell comprises the antigen binding molecule, the antigen binding molecule is chimeric antigen receptor (CAR), which comprises an antigen-binding domain, a transmembrane domain, and an intracellular signaling domain.
24. The modified cell of embodiment 23, wherein the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMW-MAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LACE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.
25. The modified cell of any one of embodiments 23 and 24, wherein the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D
26. The modified cell of any one of embodiments 1-22, wherein the modified cell comprises the antigen binding molecule, the antigen binding molecule is a modified TCR (TCR) or TCR (TIL).
27. The modified cell of embodiment 26, wherein the TCR is derived from spontaneously occurring tumor-specific T cells in patients.
28. The modified cell of embodiment 27, wherein the TCR binds to a tumor antigen.
29. The modified cell of embodiment 28, wherein the tumor antigen comprises CEA, gp100, MART-1, p53, MAGE-A3, or NY-ESO-1.
30. The modified cell of embodiment 28, wherein the TCR comprises TCRγ and TCRδ Chains or TCRα and TCRβ chains, or a combination thereof.
31. The modified cell of any of the preceding embodiments, wherein the cell is an immune effector cell (e.g., a population of immune effector cells).
32. The modified cell of embodiment 31, wherein the immune effector cell is a T cell or an NK Cell.
33. The modified cell of embodiment 32, wherein the immune effector cell is a T cell.
34. The modified cell of embodiment 32 wherein the T cell is a CD4+ T cell, a CD8+ T cell, or a combination thereof.
35. The modified cell of any of the preceding embodiments, wherein the cell is a human cell.
36. The modified cell of any of the preceding embodiments, wherein the enhanced expression and/or function of the modified component of TCR-CD3 complex is implemented by introducing a polynucleotide encoding the modified component of TCR-CD3 complex and/or the binding molecule, which is present in the modified cell in a recombinant DNA construct, in an mRNA, or in a viral vector.
37. The modified cell of embodiment 36, wherein the polynucleotide is an mRNA, which is not integrated into the genome of the modified cell.
38. The modified cell of embodiment 36, wherein the polynucleotide is associated with an oxygen-sensitive polypeptide domain.
39. The modified cell of embodiment 38, wherein the oxygen-sensitive polypeptide domain comprises HIF VHL binding domain.
40. The modified cell of embodiment 36, wherein the polynucleotide is regulated by a promoter comprising a binding site for a transcription modulator that modulates the expression and/or secretion of the therapeutic agent in the cell.
41. The modified cell of embodiment 40, wherein the transcription modulator is or includes Hif1a, NFAT, FOXP3, and/or NFkB.
42. A cell modified to express one or more molecules at a level that is higher or lower than the level of the one or more expressed by a cell that has not been modified to expression the one or more molecules, wherein the one or more molecules are associated with metabolism of the modified cell.
43. A modified cell engineered to express an antigen binding molecule, wherein expression and/or function of one or more molecules in the modified cell has been enhanced or reduced (including eliminated), where the one or more molecules are associated with metabolism of the modified cell.
44. The modified cell of any one of embodiments 42 and 43, wherein the modified cell comprises a disruption in an endogenous gene or an addition of exogenous gene that is associated with a biosynthesis or transportation pathway of the one or more molecules.
45. A method or use of polynucleotide, the method comprising providing a viral particle (e.g., AAV, lentivirus or their variants) comprising a vector genome, the vector genome comprising the polynucleotide encoding the one more molecules and a polynucleotide encoding an antigen binding molecule, the polynucleotide operably linked to an expression control element conferring transcription of the polynucleotides; and administering an amount of the viral particle to a subject such that the polynucleotide is expressed in the subject, where the one or more molecules are associated with metabolism of the modified cell.

46. The method of embodiment 45, wherein the AAV preparation may include AAV vector particles, empty capsids and host cell impurities, thereby providing an AAV product substantially free of AAV empty capsids.

47. A pharmaceutical composition comprising the population of the cells of any of embodiments 1-3.

48. A method of causing or eliciting T cell response in a subject in need thereof and/or treating a tumor of the subject, the method comprising administering an effective amount of the composition of embodiment 47 to the subject or an isolated nucleic acid sequence encoding one or more molecules associated with metabolism of the modified cell.

49. The isolated nucleic acid sequence, modified cell, method, or pharmaceutical composition of any one of embodiments 42-48, wherein the one more molecules comprise at least one of MCT1, MCT2, MCT3, LDHB, and MPC, a functional variant of the one or more molecules, or a functional fragment of the one or more molecules; and/or the metabolism comprises metabolism of lactic acid.

50. The isolated nucleic acid sequence, modified cell, method, or pharmaceutical composition of any one of embodiments 42-48, wherein the metabolism comprises transportation of lactic acid of the modified cells, which is changed.

51. The modified cell of any proceeding embodiments 42-50, wherein the modified cells transport less or more lactic acid into the modified cells than that of corresponding wild-type cells.

52. The modified cell of any proceeding embodiments 42-50, wherein the modified cells overexpress MCT 3 and express less MCT1 and MCT2, and transport less lactic acid into the modified cells than that of corresponding wild-type cells.

53. The modified cell of any proceeding embodiments 42-50, wherein the modified cells overexpress MCT1, MCT2, LDHB, and MPC, express less MCT3, and transport more lactic acid into the modified cells than that of corresponding wild-type cells.

54. The isolated nucleic acid sequence, modified cell, method, or pharmaceutical composition of any one of embodiments 42-53, wherein the one more molecules comprise at least one of Frataxin, HBA, HBB, HBD, HBE, HBG, TOMM20, and TOMM22, a functional variant of the one or more molecules, or a functional fragment of the one or more molecules; and/or the metabolism comprises metabolism of lactic acid.

55. The isolated nucleic acid sequence, modified cell, method, or pharmaceutical composition of any one of embodiments 42-54, wherein the metabolism comprises the oxidative function of mitochondria of the modified cells, which is enhanced.

56. The modified cell of any proceeding embodiments 42-55, wherein the modified cells overexpress Frataxin, HBA, HBB, HBD, HBE, HBG such as to enhances the mitochondrial oxygen storage capacity of the modified cells.

57. The modified cell of any proceeding embodiments 42-55, wherein the modified cells overexpress TOMM20 and TOMM22 such as to enhance functions of mitochondria of the modified cells.

58. The isolated nucleic acid sequence, modified cell, method, or pharmaceutical composition of any one of embodiments 42-47, wherein the one more molecules comprise at least one of CD98, SNAT1, SNAT2, ASCT2, a functional variant of the one or more molecules, or a functional fragment of the one or more molecules; and/or the metabolism comprises metabolism of amino acids.

59. The isolated nucleic acid sequence, modified cell, method, or pharmaceutical composition of any one of embodiments 42-48, wherein the metabolism comprises metabolism of lactic acid and/or amino acids of the modified cells, which is enhanced.

60. The modified cell of any proceeding embodiments 42-58, wherein the modified cells overexpress CD98, SNAT1, SNAT2, ASCT2 such as to enhances the transportation capability for the modified cells to transport the amino acids into the modified cells.

61. The isolated nucleic acid sequence, modified cell, method, or pharmaceutical composition of embodiment 42-60, wherein one or more sequences listed in Table 7, 8, and 9 are overexpressed or downregulated in the modified cell.

62. The modified cell of any of the preceding embodiments 42-61, wherein the modified cell comprises an antigen binding molecule.

63. The modified cell of embodiment 62, the antigen binding molecule is chimeric antigen receptor (CAR), which comprises an antigen-binding domain, a transmembrane domain, and an intracellular signaling domain.

64. The modified cell of embodiment 63, wherein the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMW-MAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LACE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

65. The modified cell of any one of embodiments 63 and 64, wherein the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D 66. The modified cell of embodiment 62, wherein the modified cell comprises the antigen binding molecule, the antigen binding molecule is a modified TCR (TCR) or TCR (TIL).
67. The modified cell of embodiment 65, wherein the TCR is derived from spontaneously occurring tumor-specific T cells in patients.
68. The modified cell of embodiment 67, wherein the TCR binds to a tumor antigen.
69. The modified cell of embodiment 68, wherein the tumor antigen comprises CEA, gp100, MART-1, p53, MAGE-A3, or NY-ESO-1.
70. The modified cell of embodiment 68, wherein the TCR comprises TCRγ and TCRδ Chains or TCRα and TCRβ chains, or a combination thereof.
71. The modified cell of embodiment 70, wherein the cell is an immune effector cell (e.g., a population of immune effector cells), and the immune effector cell is a DC, macrophage, T cell or an NK cell.
72. The modified cell of embodiment 71, wherein the immune effector cell is a T cell.
73. modified cell of embodiment 71 wherein the T cell is a CD4+ T cell, a CD8+ T cell, or a combination thereof.
74. The modified cell of any of the preceding embodiments 42-73, wherein the cell is a human cell.
75. The modified cell of any of the preceding embodiments 42-74, wherein the enhanced expression and/or function of the one or more molecules is implemented by introducing a nucleic acid sequence encoding the one or more molecules and/or the binding molecule, which is present in the modified cell in a recombinant DNA construct, in an mRNA, or in a viral vector.
76. The modified cell of embodiment 75, wherein the nucleic acid sequence is an mRNA, which is not integrated into the genome of the modified cell.
77. The modified cell of embodiment 75, wherein the nucleic acid sequence is associated with an oxygen-sensitive polypeptide domain.
78. The modified cell of embodiment 77, wherein the oxygen-sensitive polypeptide domain comprises HIF VHL binding domain.
79. The modified cell of embodiment 75, wherein the nucleic acid sequence is regulated by a promoter comprising a binding site for a transcription modulator that modulates the expression and/or secretion of the therapeutic agent in the cell.
80. The modified cell of embodiment 79, wherein the transcription modulator is or includes Hif1a, NFAT, FOXP3, and/or NFkB.

EXAMPLES

Lentiviral vectors that encode individual CAR molecules were generated and transfected with T cells, which are elaborated below. Techniques related to cell cultures, construction of cytotoxic T lymphocyte essay may be found in "Control of large, established tumor xenografts with genetically retargeted human T cells containing CD28 and CD137 domains," PNAS, Mar. 3, 2009, vol. 106 no. 9, 3360-3365, and "Chimeric Receptors Containing CD137 Signal Transduction Domains Mediate Enhanced Survival of T Cells and Increased Antileukemic Efficacy In Vivo," Molecular Therapy, August 2009, vol. 17 no. 8, 1453-1464, which are incorporated herein by reference in their entirety.

Figure 6:
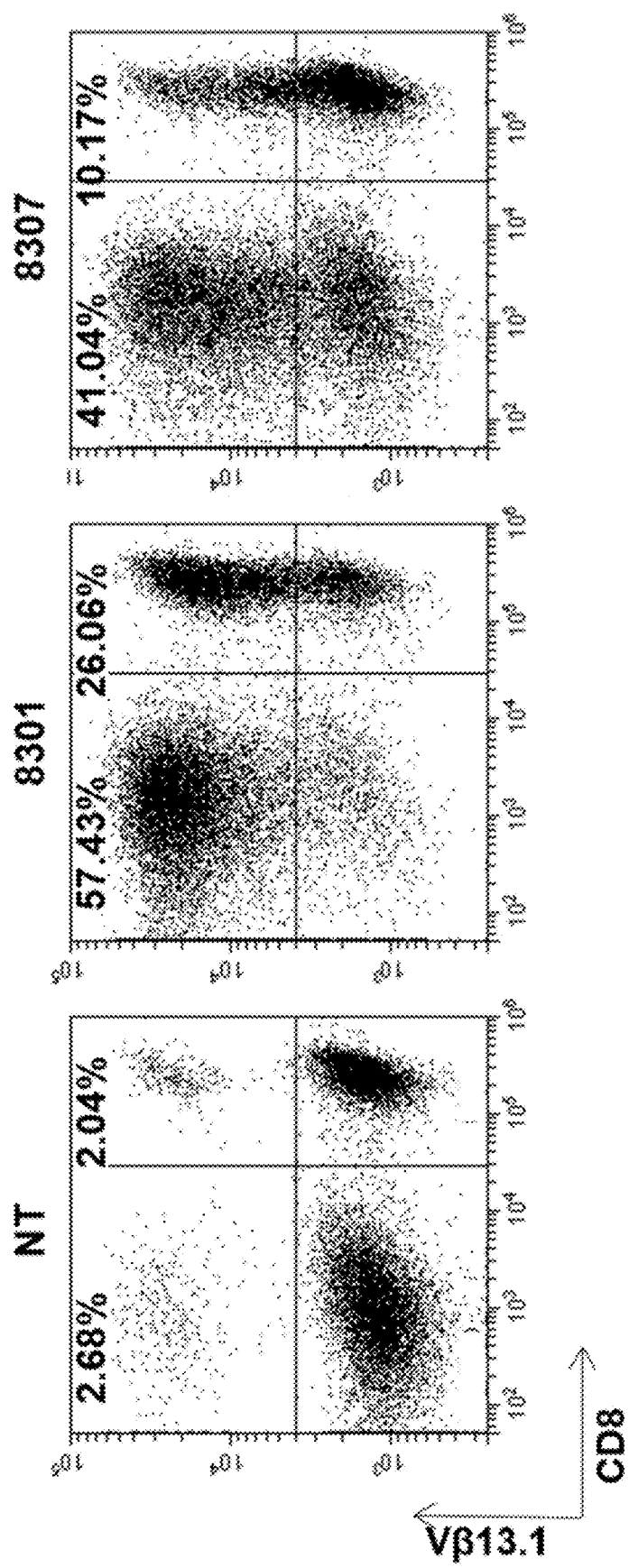
FIG. 6 shows flow cytometry results of the expression of various vectors in T cells.

On day 0, peripheral blood was extracted from healthy volunteers. CD3+T cells were sorted by pan T Kit, and 100 ul TransAct per $1\times10^7$ T cells were added. On day 1, $1\times10^6$ T cells were transfected with vector 8301. $1\times10^6$ T cells were transfected with vector 8307, and $2\times10^6$ T cells were non-transduced T cells (N.T.). On day 2, culture media were changed. The lentivirus and TransAct were removed, and the cells were resuspended in fresh media. On day 7, the flow detection of the TCR ratio was performed. FIG. 6 shows flow cytometry results of the expression of the various vectors in T cells. Since both vectors encode Vβ13.1 (a variant of the TCR β chain), the anti-TCR Vβ13.1 was used. The expression ratio of Vβ13.1 with vector 8301 is 83.58%. The expression ratio of Vβ13.1 with vector 8307 is 51.38%. The experiment was carried out according to Tables 3 and 4. The samples were co-cultured for 24h, and FCM staining of Vβ 13.1+multicolor was taken, and the amplification was detected by FCM staining with a cell trace marker at 120 h. Sequences can be found in Table 2 below. More information on sequences, compositions, and related clinical trials can be found in WO2020106843 and WO2020146743, which are hereby incorporated by reference in their entirety.

TABLE 2

| Description | | SEQ ID NO: |
|---|---|---|
| CD3 Zeta Chain | MKWKALFTAAILQAQLPITEAQSFGLLDPKLCYLLDGILFIYGVILT ALFLRVKFSRSADAPAYQQGQNQLYNELNLGRREEYDVLDKRR GRDPEMGGKPQRRKNPQEGLYNELQKDKMAEAYSEIGMKGE RRRGKGHDGLYQGLSTATKDTYDALHMQALPPR | 1 |

TABLE 2-continued

| Description | Sequence | SEQ ID NO: |
|---|---|---|
| CD3 Delta Chain | MEHSTFLSGLVLATLLSQVSPFKIPIEELEDRVFVNCNTSITWVE GTVGTLLSDITRLDLGKRILDPRGIYRCNGTDIYKDKESTVQVHY RMCQSCVELDPATVAGIIVTDVIATLLLALGVFCFAGHETGRLSG AADTQALLRNDQVYQPLRDRDDAQYSHLGGNWARNK | 2 |
| CD3 Epsilon Chain | MQSGTHWRVLGLCLLSVGVWGQDGNEEMGGITQTPYKVSISG TTVILTCPQYPGSEILWQHNDKNIGGDEDDKNIGSDEDHLSLKE FSELEQSGYYVCYPRGSKPEDANFYLYLRARVCENCMEMDVM SVATIVIVDICITGGLLLLVYYWSKNRKAKAKPVTRGAGAGGRQR GQNKERPPPVPNPDYEPIRKGQRDLYSGLNQRRI | 3 |
| CD3 gamma Chain | MEQGKGLAVLILAIILLQGTLAQSIKGNHLVKVYDYQEDGSVLLT CDAEAKNITWFKDGKMIGFLTEDKKKWNLGSNAKDPRGMYQC KGSQNKSKPLQVYYRMCQNCIELNAATISGFLFAEIVSIFVLAVG VYFIAGQDGVRQSRASDKQTLLPNDQLYQPLKDREDDQYSHLQ GNQLRRN | 4 |
| GS-Linker | SGGGGS | 5 |
| NY-ESO-1 Vα | METLLGLLILWLQLQWVSSKQEVTQIPAALSVPEGENLVLNCSF TDSAIYNLQWFRQDPGKGLTSLLLIQSSQREQTSGRLNASLDK SSGRSTLYIAASQPGDSATYLCAVRPTSGGSYIPTFGRGTSLIV HPYIQNPDDAVYQLRDSKSSDKSVCLFTDFDSQTNVSQSKDS DVYITDKTVLDMRSMDFKSNSAVAWSNKSDFACANAFNNSIIP EDTFFPSPESSCDVKLVEKSFETDTNLNFQNLSVIGFRILLLKVA GFNLLMTLRLWSS | 6 |
| P2A | GSGATNFSLLKQAGDVEENPGP | 7 |
| NY-ESO-1 Vβ | MSIGLLCCAALSLLWAGPVNAGVTQTPKFQVLKTGQSMTLQC AQDMNHEYMSWYRQDPGMGLRLIHYSVGAGITDQGEVPNGY NVSRSTTEDFPLRLLSAAPSQTSVYFCASSYVGNTGELFFGEG SRLTVLEDLKNVFPPEVAVFEPSEAEISHTQKATLVCLATGFYP DHVELSWWVNGKEVHSGVSTDPQPLKEQPALNDSRYSLSSR LRVSATFWQNPRNHFRCQVQFYGLSENDEWTQDRAKPVTQI VSAEAWGRADCGFTSESYQQGVLSATILYEILLGKATLYAVLVS ALVLMAMVKRKDSRG | 8 |
| T2A | GSGEGRGSLLTCGDVEENPGP | 9 |
| ζ-chain (full-length) | MKWKALFTAAILQAQLPITEAQSFGLLDPKLCYLLDGILFIYGVIL TALFLRVKFSRSADAPAYQQGQNQLYNELNLGRREEYDVLDK RRGRDPEMGGKPRRKNPQEGLYNELQKDKMAEAYSEIGMKG ERRRGKGHDGLYQGLSTATKDTYDALHMQALPPR | 10 |
| CD137 (intracellular) | KRGRKKLLYIFKQPFMRPVQTTQEEDGCSCRFPEEEEGGCEL | 11 |
| ζ-chain-2A-CD137 (intracellular) | MKWKALFTAAILQAQLPITEAQSFGLLDPKLCYLLDGILFIYGVIL TALFLRVKFSRSADAPAYQQGQNQLYNELNLGRREEYDVLDK RRGRDPEMGGKPRRKNPQEGLYNELQKDKMAEAYSEIGMKG ERRRGKGHDGLYQGLSTATKDTYDALHMQALPPR GSGEGRGSLLTCGDVEENPGP KRGRKKLLYIFKQPFMRPVQTTQEEDGCSCRFPEEEEGGCEL | 18 |
| NY-ESO-1 TCRα + β-2A-ζ-chain (full-length)-CD137 (intracellular) | METLLGLLILWLQLQWVSSKQEVTQIPAALSVPEGENLVLNCSF TDSAIYNLQWFRQDPGKGLTSLLLIQSSQREQTSGRLNASLDK SSGRSTLYIAASQPGDSATYLCAVRPTSGGSYIPTFGRGTSLIV HPYIQNPDDAVYQLRDSKSSDKSVCLFTDFDSQTNVSQSKDS DVYITDKTVLDMRSMDFKSNSAVAWSNKSDFACANAFNNSIIP EDTFFPSPESSCDVKLVEKSFETDTNLNFQNLSVIGFRILLLKVA GFNLLMTLRLWSSGSGATNFSLLKQAGDVEENPGPMSIGLLC CAALSLLWAGPVNAGVTQTPKFQVLKTGQSMTLQCAQDMNH EYMSWYRQDPGMGLRLIHYSVGAGITDQGEVPNGYNVSRSTT EDFPLRLLSAAPSQTSVYFCASSYVGNTGELFFGEGSRLTVLE DLKNVFPPEVAVFEPSEAEISHTQKATLVCLATGFYPDHVELS WWVNGKEVHSGVSTDPQPLKEQPALNDSRYSLSSRLRVSATF WQNPRNHFRCQVQFYGLSENDEWTQDRAKPVTQIVSAEAWG RADCGFTSESYQQGVLSATILYEILLGKATLYAVLVSALVLMAM VKRKDSRGGSGEGRGSLLTCGDVEENPGPMKWKALFTAAILQ AQLPITEAQSFGLLDPKLCYLLDGILFIYGVILTALFLRVKFSRSA DAPAYQQGQNQLYNELNLGRREEYDVLDKRRGRDPEMGGKP RRKNPQEGLYNELQKDKMAEAYSEIGMKGERRRGKGHDGLY QGLSTATKDTYDALHMQALPPRKRGRKKLLYIFKQPFMRPVQT TQEEDGCSCRFPEEEEGCEL | 19 |

TABLE 3

| Name | Construction |
|------|--------------|
| 8301 | NY-ESO-1 TCRα + β |
| 8307 | NY-ESO-1 TCRα + β-2A-ζ-chain (full-length)-CD137 (intra) (See Embodiment 102 in FIG. 1) |

TABLE 4

|      | 293T | 8505C | K19 | E:T system |
|------|------|-------|-----|------------|
| NT   | −    | −     | −   | 40 w:13.3 w No IL2 texmacs media, 400 ul resuspended |
|      | +    | −     | −   | |
|      | −    | +     | −   | |
|      | −    | −     | +   | |
| 8301 | −    | −     | −   | |
|      | +    | −     | −   | |
|      | −    | +     | −   | |
|      | −    | −     | +   | |
| 8307 | −    | −     | −   | |
|      | +    | −     | −   | |
|      | −    | +     | −   | |
|      | −    | −     | +   | |

Figure 7:
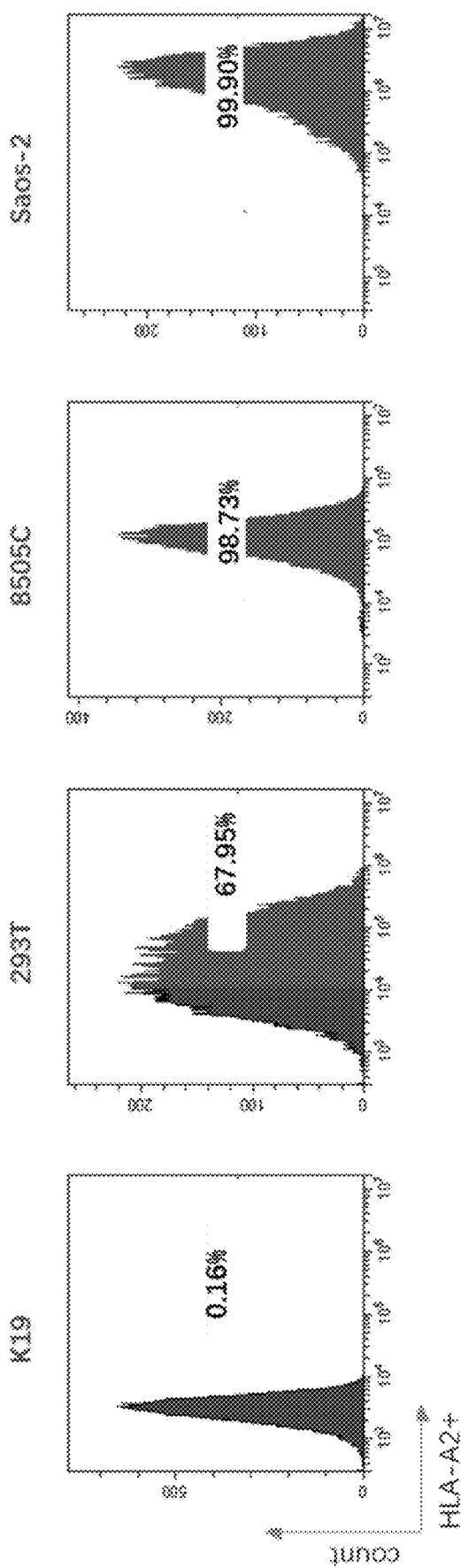
FIG. 7 shows the expression of HLA-A2 and NY-ESO-1 in substrate cells and expression of CD3ζ in these cells.
Figure 8:
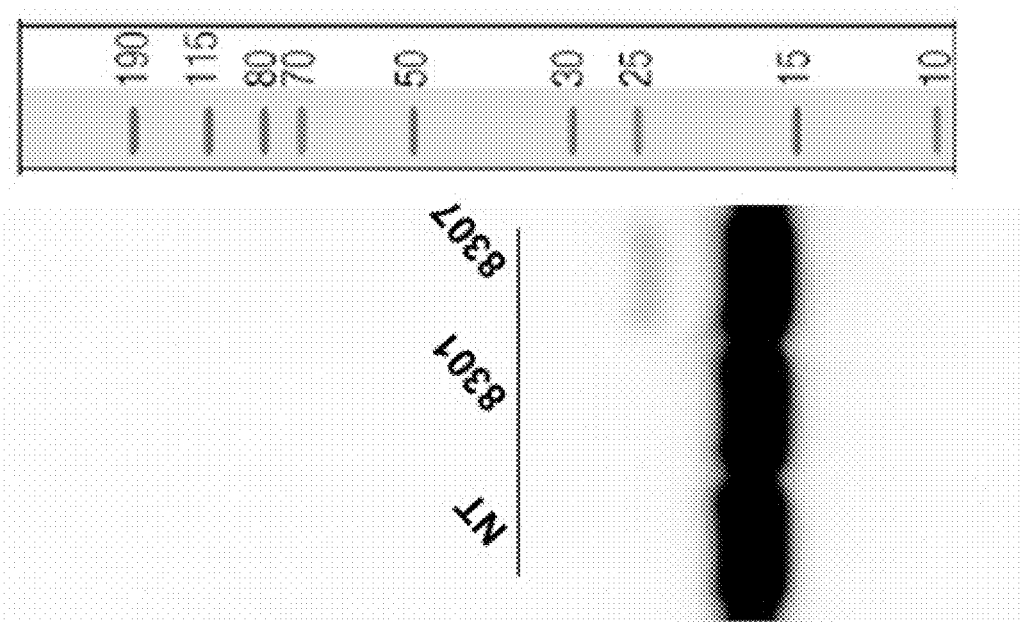
FIG. 8 shows Western blot results that confirm the structure of modified TCR.
Figure 9:
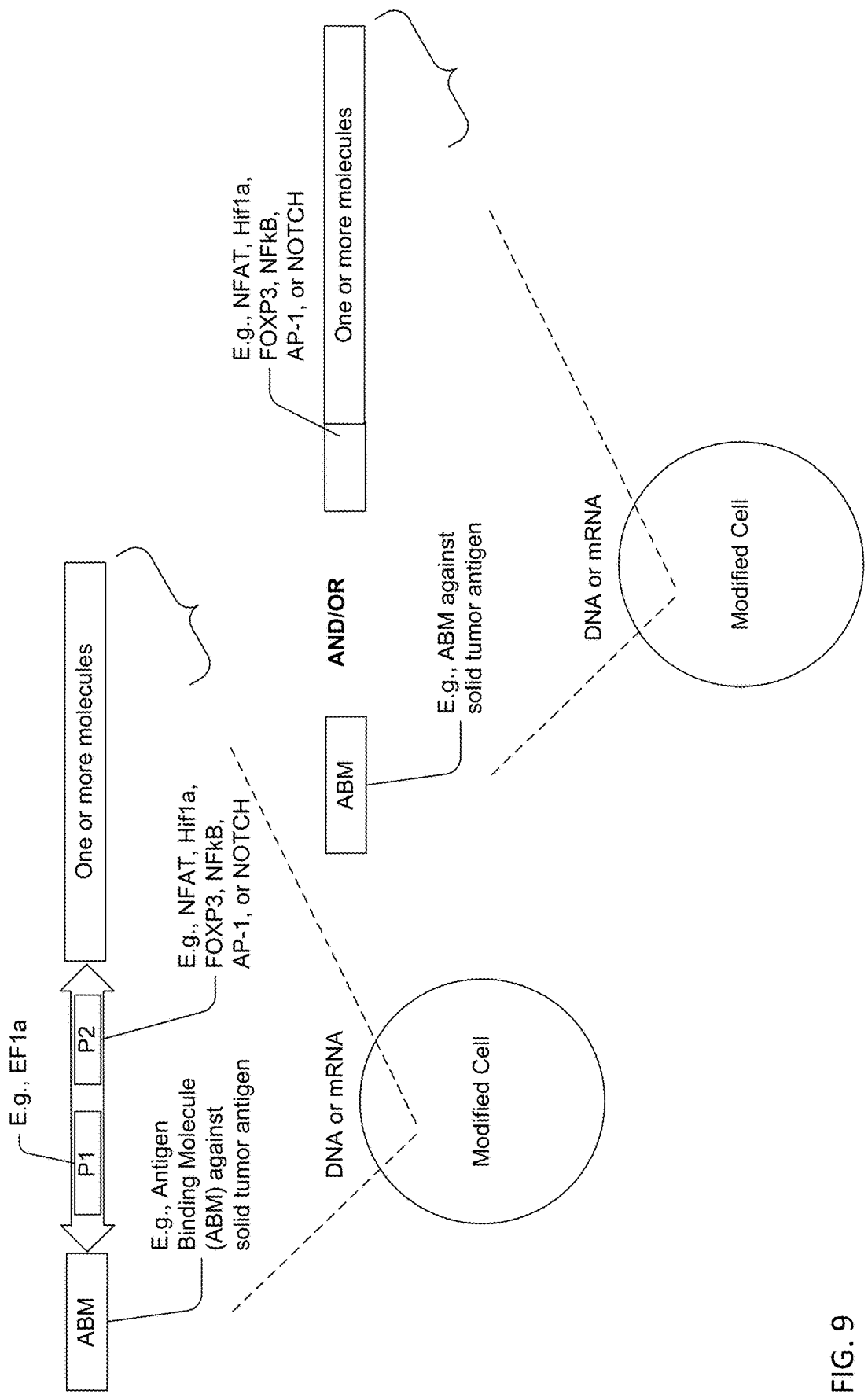
FIG. 9 shows schematic diagrams of polynucleotides and modified cells.
Figure 10:
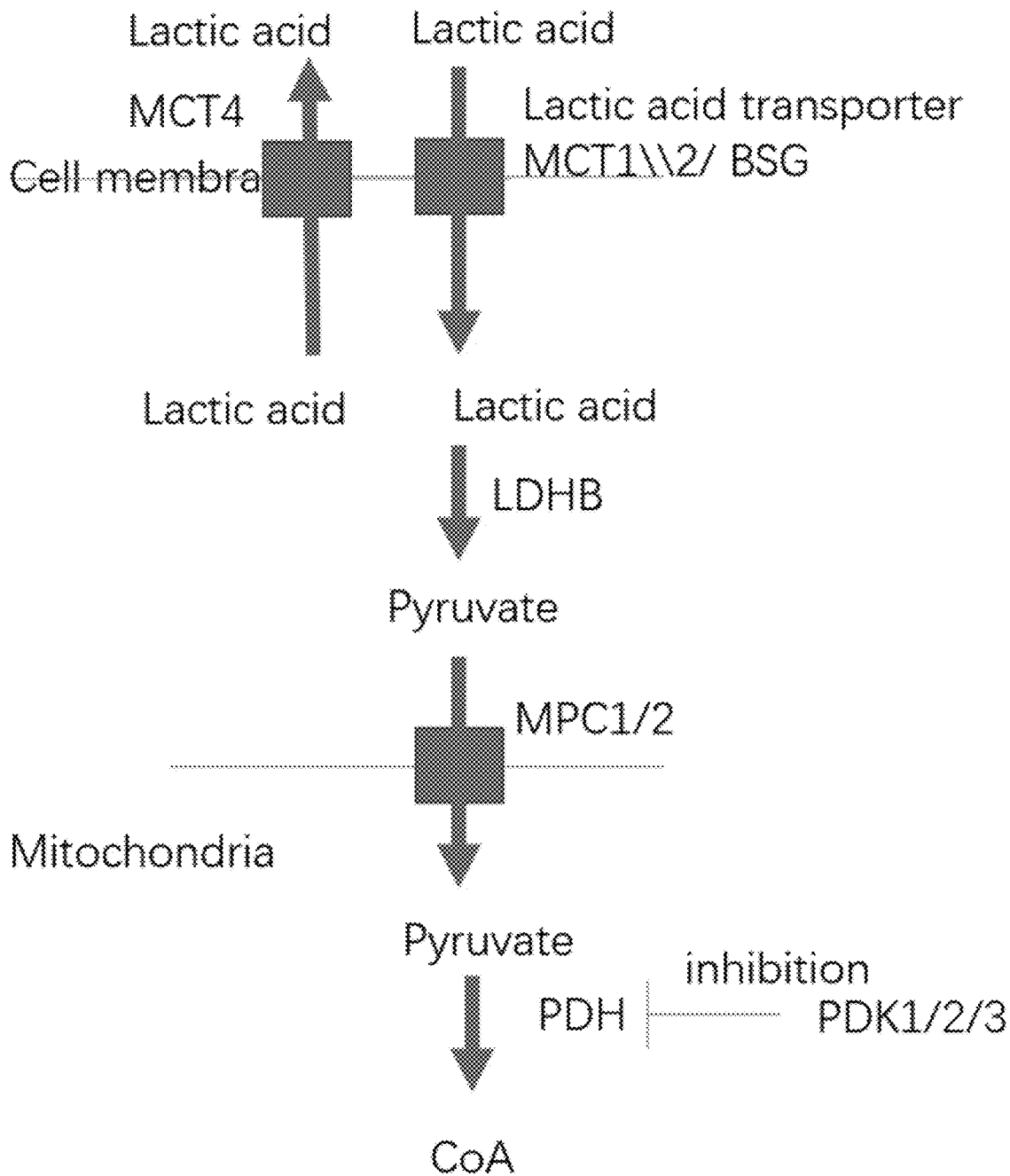
FIGS. 10, 11, 12, and 13 show schematic diagrams of metabolism processes.
Figure 11:
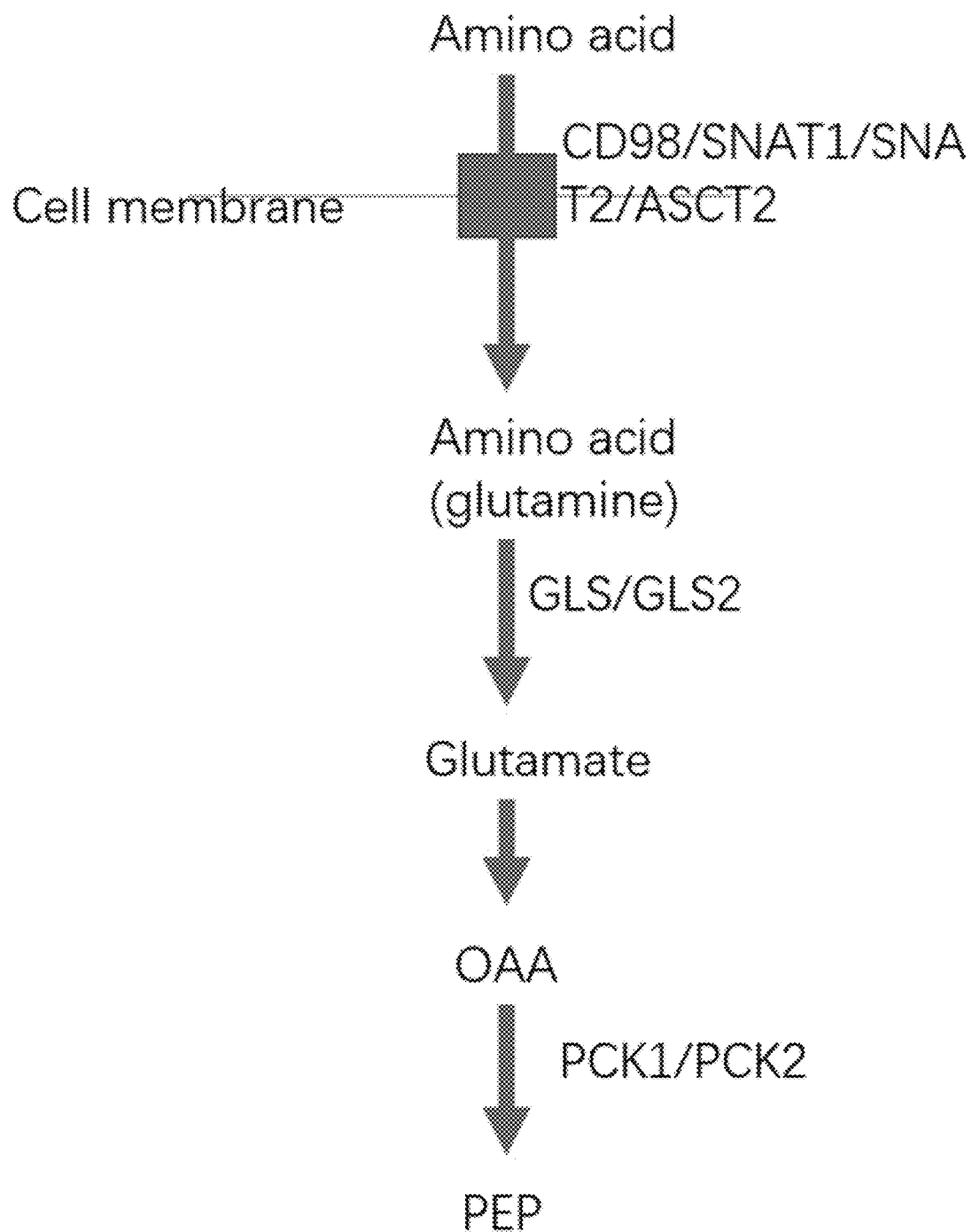
Figure 12:
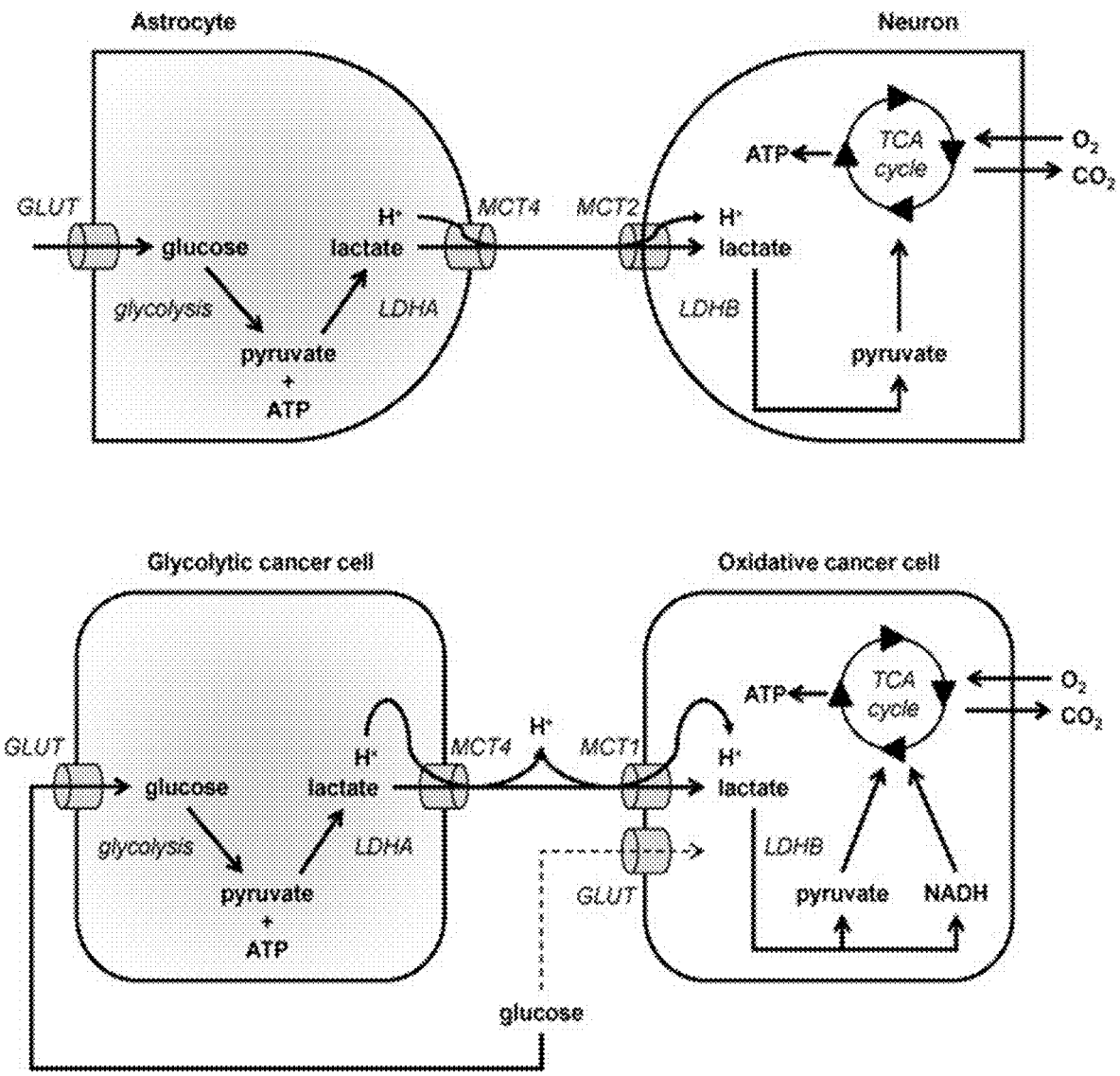
Figure 13:
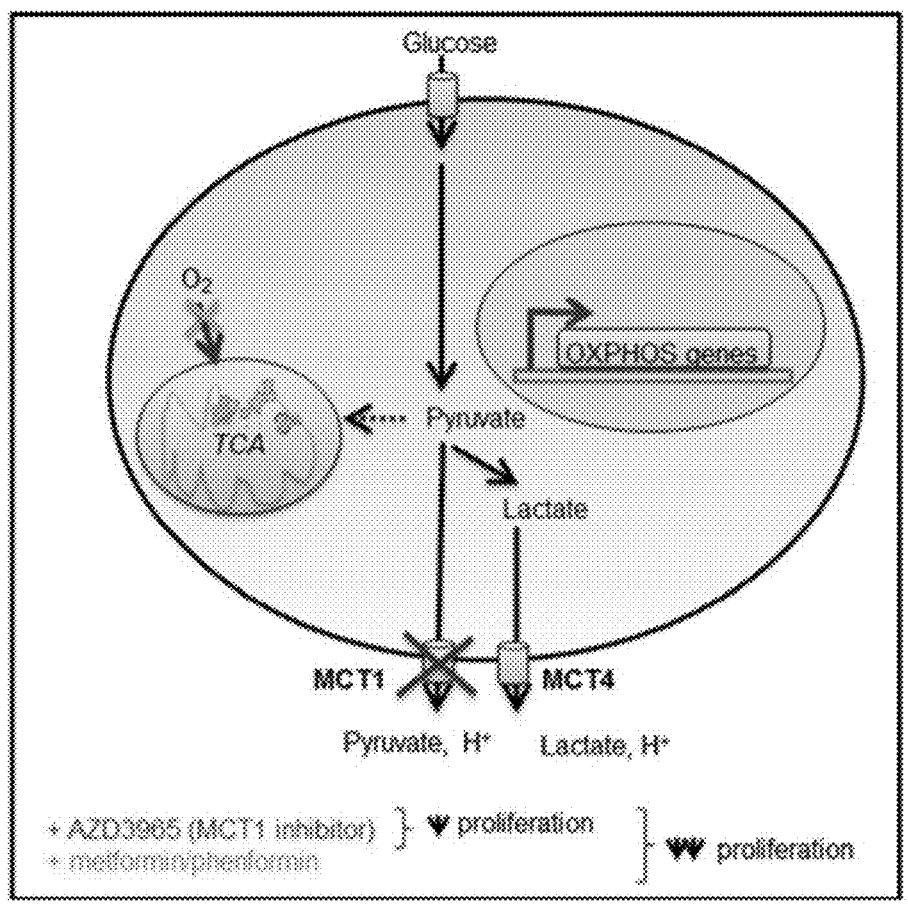
Figure 13:
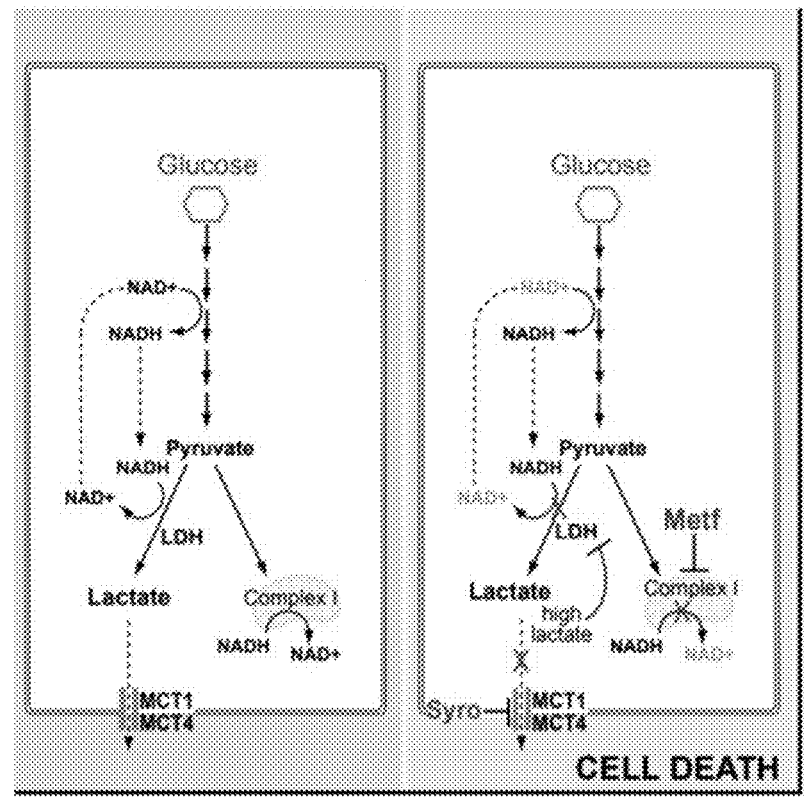

FIGS. 7 and 8 shows the expression of HLA-A2 and NY-ESO-1 in substrate cells and expression of ζ-chain in 8301 and 8307. The TCRT of NY-ESO-1, which recognizes HLA-A2 presentation, was used in the experiment as the experimental control material (8301), so the flow expression of HLA-A2 in the substrate cells was detected, and K19 appeared to be HLA-A2 negative, 293T was weak HLA-A2 positive, and 8505C, and SAOS-2 were HLA-A2 positive. RT-PCR was used to detect the mRNA expression of NY-ESO-1 in the four substrate cells, and the results showed that 8505C and SAOS-2 were positive for NY-ESO-1. The following Table 6 shows the primer information of RT-PCR. FIG. 8 shows Western blot results confirming the structure of modified TCR. Based on the Western blot results, 8307 cells have a size of about 23.3 kDa stripe, which is ζ-chain after CD137 restructuring.

TABLE 5

| number | Sample Name | ACTIN | NY-ESO-1-1 | NY-ESO-1-2 |
|--------|-------------|-------|------------|------------|
| 1 | K562   | 15.41 | 27.57 | 21.60 |
| 2 | 293T   | 15.42 | 25.57 | 30.51 |
| 3 | 8505C  | 15.59 | 22.50 | 17.88 |
| 4 | Saos-2 | 15.00 | 24.87 | 20.02 |

Ct values shown in the three rightmost columns.

TABLE 6

| Primer | Sequence (5' to 3') | SEQ ID NO |
|--------|---------------------|-----------|
| NY-ESO-1-RTF1 | CGGCAACATACTGACTATCCG | 12 |
| NY-ESO-1-RTR1 | CTGGAGACAGGAGCTGATGGA | 13 |
| NY-ESO-1-RTF2 | TGCAGACCACCGCCAACT | 14 |
| NY-ESO-1-RTR2 | TCCACATCAACAGGGAAAGCT | 15 |
| β-actin-RTF | CGCCCAGCACGATGAAA | 16 |
| β-actin-RTR | CCGCCGATCCACACAGAG | 17 |

TABLE 7

Molecules related to lactic acid metabolism

| name | Features | Method of operation |
|------|----------|---------------------|
| MCT1 is also called SLC16A1 | Normal expression on T cells, mainly regulating the inward transport of lactic acid, | Knockdown/knockout (or overexpression, combined with LDHB expression) |
| MCT2 | Lactic acid transport | Knockdown/knockout (or overexpression, combined with LDHB expression) |
| MCT4 is also called SLC16A3. | MCT4 is the transport of lactic acid out of cells, contrary to MCT1 function. However, it may also help T cells from lactic acid inhibition in a high lactic acid environment. | Overexpression or induced expression (or knockdown/knockout, combined with LDHB expression) |
| BSG (CD147) | CD147 is an accessory protein of MCT family proteins, regulating the correct localization of MCT family proteins on the cell membrane | Knockdown/knockout (or overexpression or induction of expression in combination with LDHB expression) |
| LDHB | Converting lactic acid to pyruvic acid, | Overexpression or induced expression |
| MPC1 | Pyruvate can enter the mitochondria through the pyruvate transporter (MPC) on the mitochondrial membrane. | Overexpression or induced expression |
| MPC2 | Pyruvate can enter the mitochondria through the pyruvate transporter (MPC) on the mitochondrial membrane. | Overexpression or induced expression |
| PDK1/2/3 | Pyruvate dehydrogenase kinase (PDK) inhibits PDH activity, Thereby inhibiting pyruvate metabolism | Knockout/knockdown |

TABLE 8

| | Molecules related to mitochondrial function | |
|---|---|---|
| PGC1a | Enhance mitochondrial volume and enhance oxidative phosphorylation | Overexpression or induced expression |
| OPA1 | Promote mitochondrial fusion, enhance mitochondrial function, and improve electron transport chain efficiency | " |
| HBE1 (Hemoglobin subunit epsilon) | The epsilon chain is a beta-type chain of early mammalian embryonic hemoglobin, mitochondrial protein | " |
| HBZ (Hemoglobin subunit zeta) | The zeta chain is an alpha-type chain of mammalian embryonic hemoglobin. mitochondrial protein | " |
| HBD (Hemoglobin subunit delta) | Involved in oxygen transport from the lung to the various peripheral tissues. mitochondrial protein | " |
| HBA1 (Hemoglobin subunit alpha) | Involved in oxygen transport from the lung to the various peripheral tissues. mitochondrial protein | " |
| HBB (Hemoglobin subunit beta) | Involved in oxygen transport from the lung to the various peripheral tissues. mitochondrial protein | " |
| HBG1 (Hemoglobin subunit gamma-1) | Gamma chains make up the fetal hemoglobin F, in combination with alpha chains. mitochondrial protein | " |
| HBG2 (Hemoglobin subunit gamma-2) | Gamma chains make up the fetal hemoglobin F, in combination with alpha chains. mitochondrial protein | " |
| LYRM4 (LYR motif-containing protein 4) | Required for nuclear and mitochondrial iron-sulfur protein biosynthesis. Mitochondrial protein | " |
| FXN (Frataxin, mitochondrial) | Promotes the biosynthesis of heme and assembly and repair of iron-sulfur clusters. Mitochondrial protein | " |
| TOMM20(Mitochondrial import receptor subunit TOM20 homolog) | The central component of the receptor complex responsible for the recognition and translocation of cytosolically synthesized mitochondrial preproteins. Mitochondrial assembling proteins | " |
| TOMM22(Mitochondrial import receptor subunit TOM22 homolog) | The central receptor component of the translocase of the outer membrane of mitochondria (TOM complex) responsible for the recognition and translocation of cytosolically synthesized mitochondrial preproteins. Mitochondrial assembling proteins<白 | " |
| HSPE1 (10 kDa heat shock protein, mitochondrial) | Co-chaperonin implicated in mitochondrial protein import and macromolecular assembly. Together with Hsp60, facilitates the correct folding of imported proteins. Mitochondrial assembling proteins< | " |
| HSPD1 (60 kDa heat shock protein, mitochondrial) | Chaperonin implicated in mitochondrial protein import and macromolecular assembly. Together with Hsp10, it facilitates the correct folding of imported proteins. Mitochondrial assembling proteins< | " |
| HSPA9(Stress-70 protein, mitochondrial) | Chaperone protein which plays an important role in the mitochondrial iron-sulfur cluster (ISC) biogenesis. Interacts with and stabilizes ISC cluster assembly proteins. Mitochondrial assembling proteins<白 | " |

TABLE 9

| | Molecules related to amino acid metabolism | |
|---|---|---|
| name | Features | Method of operation |
| Asct2 | Amino acid transporter | Overexpression or induced expression |
| CD98 | Amino acid transporter | Overexpression or induced expression |
| SNAT1 | Amino acid transporter | Overexpression or induced expression |
| SNAT2 | Amino acid transporter | Overexpression or induced expression |

TABLE 9-continued

Molecules related to amino acid metabolism

| name | Features | Method of operation |
|---|---|---|
| PCK1 | Conversion of OAA (oxaloacetate) to PEP (phosphoenolpyruvate) Amino acid metabolism | Overexpression or induced expression |
| PCK2 | Conversion of OAA (oxaloacetate) to PEP (phosphoenolpyruvate) Amino acid metabolism | Overexpression or induced expression |
| GLS (Glutaminase kidney isoform, mitochondrial) | Glutaminase (GLS) Converts glutamine to glutamate to support the tricarboxylic acid cycle and redox and epigenetic reactions. Glutamic enzyme | Overexpression or induced expression |
| GLS2 (Glutaminase liver isoform, mitochondrial) | Plays an important role in the regulation of glutamine catabolism. Promotes mitochondrial respiration and increases ATP generation in cells by catalyzing the synthesis of glutamate and alpha-ketoglutarate. Increases cellular anti-oxidant function via NADH and glutathione production. May play a role in preventing tumor proliferation. Glutamic enzyme | Overexpression or induced expression |

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

What is claimed is:

1. A polynucleotide comprising a sequence encoding a ζ-chain of TCR-CD3 complex linked to one or more co-stimulatory signaling domains, wherein the polynucleotide comprises a sequence encoding amino acid sequence SEQ ID NO: 18 or SEQ ID NO: 19.

2. The polynucleotide of claim 1, wherein the polynucleotide further comprises a sequence encoding a modified TCR-CD3 complex comprising TCRα, TCRβ, and one or more of CD3γ, CD3ε, or CD3δ.

3. The polynucleotide of claim 1, wherein the polynucleotide further comprises a sequence encoding a modified TCR-CD3 complex comprising TCRγ, TCRδ, and CD3γ, CD3ε, or CD3δ.

4. The polynucleotide of claim 1, wherein the one or more co-stimulatory signaling domains further comprise one or more functional signaling domains of one or more proteins comprising CD27, CD28, OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG (Cbp), NKp44, NKp30, NKp46, NKG2D, or a combination thereof.

5. The polynucleotide of claim 1, wherein the one or more co-stimulatory signaling domains further comprise a functional signaling domain of CD28.

6. A vector comprising the polynucleotide of claim 1.

7. A modified cell comprising the polynucleotide of claim 1.

8. The modified cell of claim 7, wherein the modified cell comprises a chimeric antigen receptor (CAR) comprising an antigen-binding domain, a transmembrane domain, and an intracellular signaling domain.

9. The modified cell of claim 8, wherein the antigen-binding domain binds a tumor antigen comprising TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, surviving, telomerase, PCTA (Galectin 8), MelanA (MART1), Ras mutant, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase (hTERT), RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, or IGLL1.

10. The modified cell of claim 8, wherein the intracellular signaling domain further comprises a co-stimulatory signaling domain comprising one or more functional signaling domain of one or more proteins comprising CD27, CD28, OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG (Cbp), NKp44, NKp30, NKp46, NKG2D, or a combination thereof.

11. The modified cell of claim 7, wherein the modified cell comprises an antigen binding molecule, the antigen binding molecule is a modified TCR.

12. The modified cell of claim 11, wherein the TCR is derived from spontaneously occurring tumor-specific T cells in patients.

13. The modified cell of claim 12, wherein the TCR binds a tumor antigen.

14. The modified cell of claim 13, wherein the tumor antigen comprises CEA, gp100, MART-1, p53, MAGE-A3, or NY-ESO-1.

15. The modified cell of claim 11, wherein the TCR comprises TCRγ and TCRδ chains, or TCRα and TCRβ chains, or a combination thereof.

16. The modified cell claim 7, wherein the cell is an immune effector cell.

17. The modified cell of claim 16, wherein the immune effector cell is a T cell or an NK cell.

18. The modified cell of claim 17, wherein the immune effector cell is a T cell.

* * * * *

SEQUENCE LISTING

```
<160> NUMBER OF SEQ ID NOS: 19

<210> SEQ ID NO 1
<211> LENGTH: 164
<212> TYPE: PRT
<213> ORGANISM: Homo sapiens

<400> SEQUENCE: 1

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 2
<211> LENGTH: 171
<212> TYPE: PRT
<213> ORGANISM: Homo sapiens
```

```
<400> SEQUENCE: 2

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 3
<211> LENGTH: 207
<212> TYPE: PRT
<213> ORGANISM: Homo sapiens

<400> SEQUENCE: 3

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175
```

```
Lys Glu Arg Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 4
<211> LENGTH: 182
<212> TYPE: PRT
<213> ORGANISM: Homo sapiens

<400> SEQUENCE: 4

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 5
<211> LENGTH: 6
<212> TYPE: PRT
<213> ORGANISM: Homo sapiens

<400> SEQUENCE: 5

Ser Gly Gly Gly Gly Ser
1               5

<210> SEQ ID NO 6
<211> LENGTH: 274
<212> TYPE: PRT
<213> ORGANISM: Homo sapiens

<400> SEQUENCE: 6

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45
```

```
Ile Tyr Asn Leu Gln Trp Phe Arg Gln Asp Pro Gly Lys Gly Leu Thr
    50                  55                  60
Ser Leu Leu Leu Ile Gln Ser Ser Gln Arg Glu Gln Thr Ser Gly Arg
 65                  70                  75                  80
Leu Asn Ala Ser Leu Asp Lys Ser Ser Gly Arg Ser Thr Leu Tyr Ile
                 85                  90                  95
Ala Ala Ser Gln Pro Gly Asp Ser Ala Thr Tyr Leu Cys Ala Val Arg
                100                 105                 110
Pro Thr Ser Gly Gly Ser Tyr Ile Pro Thr Phe Gly Arg Gly Thr Ser
                115                 120                 125
Leu Ile Val His Pro Tyr Ile Gln Asn Pro Asp Pro Ala Val Tyr Gln
    130                 135                 140
Leu Arg Asp Ser Lys Ser Ser Asp Lys Ser Val Cys Leu Phe Thr Asp
145                 150                 155                 160
Phe Asp Ser Gln Thr Asn Val Ser Gln Ser Lys Asp Ser Asp Val Tyr
                165                 170                 175
Ile Thr Asp Lys Thr Val Leu Asp Met Arg Ser Met Asp Phe Lys Ser
                180                 185                 190
Asn Ser Ala Val Ala Trp Ser Asn Lys Ser Asp Phe Ala Cys Ala Asn
    195                 200                 205
Ala Phe Asn Asn Ser Ile Ile Pro Glu Asp Thr Phe Phe Pro Ser Pro
    210                 215                 220
Glu Ser Ser Cys Asp Val Lys Leu Val Glu Lys Ser Phe Glu Thr Asp
225                 230                 235                 240
Thr Asn Leu Asn Phe Gln Asn Leu Ser Val Ile Gly Phe Arg Ile Leu
                245                 250                 255
Leu Leu Lys Val Ala Gly Phe Asn Leu Leu Met Thr Leu Arg Leu Trp
                260                 265                 270
Ser Ser

<210> SEQ ID NO 7
<211> LENGTH: 22
<212> TYPE: PRT
<213> ORGANISM: Homo sapiens

<400> SEQUENCE: 7

Gly Ser Gly Ala Thr Asn Phe Ser Leu Leu Lys Gln Ala Gly Asp Val
 1               5                  10                  15
Glu Glu Asn Pro Gly Pro
                20

<210> SEQ ID NO 8
<211> LENGTH: 311
<212> TYPE: PRT
<213> ORGANISM: Homo sapiens

<400> SEQUENCE: 8

Met Ser Ile Gly Leu Leu Cys Cys Ala Ala Leu Ser Leu Leu Trp Ala
 1               5                  10                  15
Gly Pro Val Asn Ala Gly Val Thr Gln Thr Pro Lys Phe Gln Val Leu
                20                  25                  30
Lys Thr Gly Gln Ser Met Thr Leu Gln Cys Ala Gln Asp Met Asn His
            35                  40                  45
Glu Tyr Met Ser Trp Tyr Arg Gln Asp Pro Gly Met Gly Leu Arg Leu
    50                  55                  60
```

-continued

Ile His Tyr Ser Val Gly Ala Gly Ile Thr Asp Gln Gly Glu Val Pro
 65                  70                  75                  80

Asn Gly Tyr Asn Val Ser Arg Ser Thr Thr Glu Asp Phe Pro Leu Arg
                 85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Ser Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Ser Arg Gly
305                 310

<210> SEQ ID NO 9
<211> LENGTH: 21
<212> TYPE: PRT
<213> ORGANISM: Homo sapiens

<400> SEQUENCE: 9

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 10
<211> LENGTH: 163
<212> TYPE: PRT
<213> ORGANISM: Homo sapiens

<400> SEQUENCE: 10

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
        50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Gly Arg Asp Pro Glu Met
                85                  90                  95

Gly Gly Lys Pro Arg Arg Lys Asn Pro Gln Glu Gly Leu Tyr Asn Glu
                100                 105                 110

Leu Gln Lys Asp Lys Met Ala Glu Ala Tyr Ser Glu Ile Gly Met Lys
            115                 120                 125

Gly Glu Arg Arg Arg Gly Lys Gly His Asp Gly Leu Tyr Gln Gly Leu
        130                 135                 140

Ser Thr Ala Thr Lys Asp Thr Tyr Asp Ala Leu His Met Gln Ala Leu
145                 150                 155                 160

Pro Pro Arg

<210> SEQ ID NO 11
<211> LENGTH: 42
<212> TYPE: PRT
<213> ORGANISM: Homo sapiens

<400> SEQUENCE: 11

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 12
<211> LENGTH: 21
<212> TYPE: DNA
<213> ORGANISM: Artificial Sequence
<220> FEATURE:
<223> OTHER INFORMATION: Synthesized

<400> SEQUENCE: 12
cggcaacata ctgactatcc g                                          21

<210> SEQ ID NO 13
<211> LENGTH: 21
<212> TYPE: DNA
<213> ORGANISM: Artificial Sequence
<220> FEATURE:
<223> OTHER INFORMATION: Synthesized

<400> SEQUENCE: 13
ctggagacag gagctgatgg a                                          21

<210> SEQ ID NO 14
<211> LENGTH: 18
<212> TYPE: DNA
<213> ORGANISM: Artificial Sequence
<220> FEATURE:
<223> OTHER INFORMATION: Synthesized

<400> SEQUENCE: 14
tgcagaccac cgccaact                                              18

```
<210> SEQ ID NO 15
<211> LENGTH: 21
<212> TYPE: DNA
<213> ORGANISM: Artificial Sequence
<220> FEATURE:
<223> OTHER INFORMATION: Synthesized

<400> SEQUENCE: 15
tccacatcaa cagggaaagc t                                              21

<210> SEQ ID NO 16
<211> LENGTH: 17
<212> TYPE: DNA
<213> ORGANISM: Artificial Sequence
<220> FEATURE:
<223> OTHER INFORMATION: Synthesized

<400> SEQUENCE: 16
cgcccagcac gatgaaa                                                   17

<210> SEQ ID NO 17
<211> LENGTH: 18
<212> TYPE: DNA
<213> ORGANISM: Artificial Sequence
<220> FEATURE:
<223> OTHER INFORMATION: Synthesized

<400> SEQUENCE: 17
ccgccgatcc acacagag                                                  18

<210> SEQ ID NO 18
<211> LENGTH: 226
<212> TYPE: PRT
<213> ORGANISM: Artificial Sequence
<220> FEATURE:
<223> OTHER INFORMATION: Synthesized

<400> SEQUENCE: 18

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140

Ser Thr Ala Thr Lys Asp Thr Tyr Asp Ala Leu His Met Gln Ala Leu
145                 150                 155                 160

Pro Pro Arg Gly Ser Gly Glu Gly Arg Gly Ser Leu Leu Thr Cys Gly
                165                 170                 175
```

```
Asp Val Glu Glu Asn Pro Gly Pro Lys Arg Gly Arg Lys Leu Leu
            180                 185                 190

Tyr Ile Phe Lys Gln Pro Phe Met Arg Pro Val Gln Thr Thr Gln Glu
        195                 200                 205

Glu Asp Gly Cys Ser Cys Arg Phe Pro Glu Glu Glu Gly Gly Cys
210                 215                 220

Glu Leu
225

<210> SEQ ID NO 19
<211> LENGTH: 833
<212> TYPE: PRT
<213> ORGANISM: Artificial Sequence
<220> FEATURE:
<223> OTHER INFORMATION: Synthesized

<400> SEQUENCE: 19

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Thr Ser Gly Gly Ser Tyr Ile Pro Thr Phe Gly Arg Gly Thr Ser
        115                 120                 125

Leu Ile Val His Pro Tyr Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser Gly Ser Gly Ala Thr Asn Phe Ser Leu Leu Lys Gln Ala Gly
        275                 280                 285

Asp Val Glu Glu Asn Pro Gly Pro Met Ser Ile Gly Leu Leu Cys Cys
    290                 295                 300
```

-continued

Ala Ala Leu Ser Leu Leu Trp Ala Gly Pro Val Asn Ala Gly Val Thr
305                 310                 315                 320

Gln Thr Pro Lys Phe Gln Val Leu Lys Thr Gly Gln Ser Met Thr Leu
            325                 330                 335

Gln Cys Ala Gln Asp Met Asn His Glu Tyr Met Ser Trp Tyr Arg Gln
            340                 345                 350

Asp Pro Gly Met Gly Leu Arg Leu Ile His Tyr Ser Val Gly Ala Gly
            355                 360                 365

Ile Thr Asp Gln Gly Glu Val Pro Asn Gly Tyr Asn Val Ser Arg Ser
370                 375                 380

Thr Thr Glu Asp Phe Pro Leu Arg Leu Leu Ser Ala Ala Pro Ser Gln
385                 390                 395                 400

Thr Ser Val Tyr Phe Cys Ala Ser Ser Tyr Val Gly Asn Thr Gly Glu
            405                 410                 415

Leu Phe Phe Gly Glu Gly Ser Arg Leu Thr Val Leu Glu Asp Leu Lys
            420                 425                 430

Asn Val Phe Pro Pro Glu Val Ala Val Phe Glu Pro Ser Glu Ala Glu
            435                 440                 445

Ile Ser His Thr Gln Lys Ala Thr Leu Val Cys Leu Ala Thr Gly Phe
            450                 455                 460

Tyr Pro Asp His Val Glu Leu Ser Trp Trp Val Asn Gly Lys Glu Val
465                 470                 475                 480

His Ser Gly Val Ser Thr Asp Pro Gln Pro Leu Lys Glu Gln Pro Ala
            485                 490                 495

Leu Asn Asp Ser Arg Tyr Ser Leu Ser Ser Arg Leu Arg Val Ser Ala
            500                 505                 510

Thr Phe Trp Gln Asn Pro Arg Asn His Phe Arg Cys Gln Val Gln Phe
            515                 520                 525

Tyr Gly Leu Ser Glu Asn Asp Glu Trp Thr Gln Asp Arg Ala Lys Pro
530                 535                 540

Val Thr Gln Ile Val Ser Ala Glu Ala Trp Gly Arg Ala Asp Cys Gly
545                 550                 555                 560

Phe Thr Ser Glu Ser Tyr Gln Gln Gly Val Leu Ser Ala Thr Ile Leu
            565                 570                 575

Tyr Glu Ile Leu Leu Gly Lys Ala Thr Leu Tyr Ala Val Leu Val Ser
            580                 585                 590

Ala Leu Val Leu Met Ala Met Val Lys Arg Lys Asp Ser Arg Gly Gly
            595                 600                 605

Ser Gly Glu Gly Arg Gly Ser Leu Leu Thr Cys Gly Asp Val Glu Glu
            610                 615                 620

Asn Pro Gly Pro Met Lys Trp Lys Ala Leu Phe Thr Ala Ala Ile Leu
625                 630                 635                 640

Gln Ala Gln Leu Pro Ile Thr Glu Ala Gln Ser Phe Gly Leu Leu Asp
            645                 650                 655

Pro Lys Leu Cys Tyr Leu Leu Asp Gly Ile Leu Phe Ile Tyr Gly Val
            660                 665                 670

Ile Leu Thr Ala Leu Phe Leu Arg Val Lys Phe Ser Arg Ser Ala Asp
            675                 680                 685

Ala Pro Ala Tyr Gln Gln Gly Gln Asn Gln Leu Tyr Asn Glu Leu Asn
            690                 695                 700

Leu Gly Arg Arg Glu Glu Tyr Asp Val Leu Asp Lys Arg Arg Gly Arg
705                 710                 715                 720

-continued

```
Asp Pro Glu Met Gly Gly Lys Pro Arg Arg Lys Asn Pro Gln Glu Gly
                725                 730                 735
Leu Tyr Asn Glu Leu Gln Lys Asp Lys Met Ala Glu Ala Tyr Ser Glu
                740                 745                 750
Ile Gly Met Lys Gly Glu Arg Arg Arg Gly Lys Gly His Asp Gly Leu
                755                 760                 765
Tyr Gln Gly Leu Ser Thr Ala Thr Lys Asp Thr Tyr Asp Ala Leu His
            770                 775                 780
Met Gln Ala Leu Pro Pro Arg Lys Arg Gly Arg Lys Lys Leu Leu Tyr
785                 790                 795                 800
Ile Phe Lys Gln Pro Phe Met Arg Pro Val Gln Thr Thr Gln Glu Glu
                805                 810                 815
Asp Gly Cys Ser Cys Arg Phe Pro Glu Glu Glu Glu Gly Gly Cys Glu
                820                 825                 830
Leu
```